(12) United States Patent
Boitano et al.

(10) Patent No.: US 11,952,379 B2
(45) Date of Patent: Apr. 9, 2024

(54) SMALL MOLECULE MODULATORS OF PAR2 AND USES THEREOF

(71) Applicants: Arizona Board of Regents on Behalf of the University of Arizona, Tucson, AZ (US); Board of Regents, The University of Texas System, Austin, TX (US)

(72) Inventors: Scott A. Boitano, Tucson, AZ (US); Josef Vagner, Tucson, AZ (US); Theodore J. Price, Austin, TX (US); Greg Dussor, Austin, TX (US)

(73) Assignees: Arizona Board of Regents on Behalf of the University of Arizona, Tucson, AZ (US); Board of Regents, The University of Texas System, Austin, TX (US)

( * ) Notice: Subject to any disclaimer, the term of this patent is extended or adjusted under 35 U.S.C. 154(b) by 672 days.

(21) Appl. No.: 17/046,633

(22) PCT Filed: Apr. 9, 2019

(86) PCT No.: PCT/US2019/026553
§ 371 (c)(1),
(2) Date: Oct. 9, 2020

(87) PCT Pub. No.: WO2019/199800
PCT Pub. Date: Oct. 17, 2019

(65) Prior Publication Data
US 2021/0107909 A1 Apr. 15, 2021

Related U.S. Application Data

(60) Provisional application No. 62/654,969, filed on Apr. 9, 2018.

(51) Int. Cl.
*C07D 487/04* (2006.01)
*C07D 241/36* (2006.01)
*C07D 487/14* (2006.01)
*C07D 498/14* (2006.01)
*A61K 45/06* (2006.01)

(52) U.S. Cl.
CPC ......... *C07D 487/04* (2013.01); *C07D 487/14* (2013.01); *C07D 498/14* (2013.01); *A61K 45/06* (2013.01)

(58) Field of Classification Search
CPC .................. C07D 487/04; C07D 241/36
See application file for complete search history.

(56) References Cited

FOREIGN PATENT DOCUMENTS

WO WO 2017/173347 A1 10/2017

OTHER PUBLICATIONS

Eguchi et al. Tetrahedron Letters vol. 42, 2001. pp. 1237-1239.*
Adams, M.N., et al., Structure, function and pathophysiology of protease activated receptors. Pharmacol Ther 2011;130:248-82.
Asiedu, M.N. et al., Spinal protein kinase M $\zeta$ underlies the maintenance mechanism of persistent nociceptive sensitization. J Neurosci. May 4, 2011;31(18):6646-53.
Bao, Y, et al., Protease-activated receptor 2 signalling pathways: a role in pain processing. Expert Opin Ther Targets. Jan. 2014;18(1):15-27.
Bao, Y. et al., PAR2-mediated upregulation of BDNF contributes to central sensitization in bone cancer pain. Mol Pain. May 5, 2014;10:28.
Boitano, S, et al. Development and evaluation of small peptidomimetic ligands to protease-activated receptor-2 (PAR2) through the use of lipid tethering. PLoS One. Jun. 13, 2014;9(6):e99140.
Boitano, S. et al., Potent agonists of the protease activated receptor 2 (PAR2). J Med Chem. Mar. 10, 2011;54(5):1308-13.
Boitano, S., et al. The novel PAR2 ligand C391 blocks multiple PAR2 signalling pathways in vitro and in vivo. Br J Pharmacol. Sep. 2015;172(18):4535-4545.
Bunnett, N. W. Protease-activated receptors: how proteases signal to cells to cause inflammation and pain. Semin Thromb Hemost. Apr. 2006;32 Suppl 1:39-48.
Cattaruzza, F. et al., Cathepsin S Is Activated During Colitis and Causes Visceral Hyperalgesia by a PAR2-Dependent Mechanism in Mice. vol. 141, Issue 5, Nov. 2011, pp. 1864-1874.e3.
Cenac, N. et al., Role for protease activity in visceral pain in irritable bowel syndrome. J Clin Invest. Mar. 2007;117(3):636-47.
Dai, Y, et al., Proteinase-activated receptor 2-mediated potentiation of transient receptor potential vanilloid subfamily 1 activity reveals a mechanism for proteinase-induced inflammatory pain. J Neurosci. May 5, 2004;24(18):4293-9.
Flynn, A.N. et al., The protease-activated receptor-2-specific agonists 2-aminothiazol-4-yl-LIGRL-NH2 and 6-aminonicotinyl-LIGRL-NH2 stimulate multiple signaling pathways to induce physiological responses in vitro and in vivo. J Biol Chem. May 27, 2011;286(21):19076-88.
Goh, F.G., et al., Dual effect of the novel peptide antagonist K-14585 on proteinase-activated receptor-2-mediated signalling. Br J Pharmacol. Dec. 2009;158(7):1695-704.
Grant, A.D., et al., Protease-activated receptor 2 sensitizes the transient receptor potential vanilloid 4 ion channel to cause mechanical hyperalgesia in mice. J Physiol 2007; 578:715-33.
Hansen, K.K., et al. Proteinases as hormones: targets and mechanisms for proteolytic signaling. Biol Chem. Aug. 2008;389(8):971-82.
Hollenberg, M.D., et al., Biased signalling and proteinase-activated receptors (PARs): targeting inflammatory disease. Br J Pharmacol. Mar. 2014;171(5):1180-94.
Jacquet, A. Interactions of airway epithelium with protease allergens in the allergic response. Clin Exp Allergy. Mar. 2011;41(3):305-11.

(Continued)

*Primary Examiner* — Samira J Jean-Louis
(74) *Attorney, Agent, or Firm* — Casimir Jones, S.C.; Robert A. Goetz

(57) ABSTRACT

This invention is in the field of medicinal pharmacology. In particular, the invention relates to a new class of small-molecules having a pyrazino-pyrimidine-dione (or related) structure which function as modulators (activators, inhibitors) of protease activated receptor type 2 (PAR2), and their use as therapeutics for the treatment of conditions involving PAR2 activity (e.g., asthma, chronic pain, cancer and/or vascular disorders).

22 Claims, 6 Drawing Sheets

(56) References Cited

OTHER PUBLICATIONS

Kawabata, A. et al., Suppression of pancreatitis-related allodynia/hyperalgesia by proteinase-activated receptor-2 in mice. Br J Pharmacol. May 2006;148(1):54-60.

Lam, D.K. et al., Serine proteases and protease-activated receptor 2-dependent allodynia: a novel cancer pain pathway. Pain. May 2010;149(2):263-72.

Lam, D.K., et al., Novel animal models of acute and chronic cancer pain: a pivotal role for PAR2. J Neurosci. Oct. 10, 2012;32(41):14178-83.

Liu, Q, et al., The distinct roles of two GPCRs, MrgprC11 and PAR2, in itch and hyperalgesia. Sci Signal. Jul. 12, 2011;4(181):ra45.

Liu, S. et al., Protease-activated receptor 2 in dorsal root ganglion contributes to peripheral sensitization of bone cancer pain. Eur J Pain. Mar. 2014;18(3):326-37.

McGuire, J.J., et al., 2-furoyl-LIGRLO-amide: a potent and selective proteinase-activated receptor 2 agonist. J Pharmacol Exp Ther. Jun. 2004;309(3):1124-31.

Melemedjian, O.K. et al., BDNF regulates atypical PKC at spinal synapses to initiate and maintain a centralized chronic pain state. Mol Pain. Mar. 20, 2013;9:12.

Melemedjian, O.K. et al., IL-6- and NGF-induced rapid control of protein synthesis and nociceptive plasticity via convergent signaling to the eIF4F complex. J Neurosci. Nov. 10, 2010;30(45):15113-23.

Melemedjian, O.K. et al., Local translation and retrograde axonal transport of CREB regulates IL-6-induced nociceptive plasticity. Mol Pain. Jul. 4, 2014;10:45.

Ossovskaya, V.S. et al., Protease-activated receptors: contribution to physiology and disease. Physiol Rev. Apr. 2004;84(2):579-621.

Peters, T. et al., Protease-activated receptors and prostaglandins in inflammatory lung disease. Br J Pharmacol. Oct. 2009;158(4):1017-33.

Pubchem, Substance Record for SID 241072383. Availiable date: Feb. 15, 2015. [retrieved on Jul. 11, 2019]. Retrieved from the internet: <https://pubchem.ncbi.nim.nih.gov/substance/241072383>, entire document. 5 pages.

Ramachandran, R, et al., Targeting proteinase-activated receptors: therapeutic potential and challenges. Nat Rev Drug Discov. Jan. 3, 2012;11(1):69-86.

Ramachandran, R. Proteinases and signalling: pathophysiological and therapeutic implications via PARs and more. Br J Pharmacol. Mar. 2008;153 Suppl 1(Suppl 1):S263-82.

Reed, CE, et al., The role of protease activation of inflammation in allergic respiratory diseases. J Allergy Clin Immunol. Nov. 2004;114(5):997-1008; quiz 1009.

Reichling, D.B., et al., Critical role of nociceptor plasticity in chronic pain. Trends Neurosci. Dec. 2009;32(12):611-8.

Roman, K. et al., Tryptase-PAR2 axis in experimental autoimmune prostatitis, a model for chronic pelvic pain syndrome. Pain. Jul. 2014;155(7):1328-38.

Snelgrove, RJ, et al., Alternaria-derived serine protease activity drives IL-33-mediated asthma exacerbations. J Allergy Clin Immunol. Sep. 2014;134(3):583-592.e6.

Soreide, K. Proteinase-activated receptor 2 (PAR-2) in gastrointestinal and pancreatic pathophysiology, inflammation and neoplasia. Scand J Gastroenterol. Aug. 2008;43(8):902-9.

Suen, J. Y., Modulating human proteinase activated receptor 2 with a novel antagonist (GB88) and agonist (GB110). Br J Pharmacol. Mar. 2012;165(5):1413-23.

Suen, J.Y., et al., Pathway-selective antagonism of proteinase activated receptor 2. Br J Pharmacol. Sep. 2014;171(17):4112-24.

Tillu, D.V. et al. Protease-activated receptor 2 activation is sufficient to induce the transition to a chronic pain state. Pain. May 2015;156(5):859-67.

Vergnolle, N. et al., Protease-activated receptors as drug targets in inflammation and pain. Pharmacol Ther. Sep. 2009;123(3):292-309.

Vergnolle, N. et al., Proteinase-activated receptor-2 and hyperalgesia: A novel pain pathway. Nat Med. Jul. 2001;7(7):821-6.

Yau, MK, et al., Toward drugs for protease-activated receptor 2 (PAR2). J Med Chem. Oct. 10, 2013;56(19):7477-97.

Zhang, W. et al., Proteinase-activated receptor 2 mediates thermal hyperalgesia and is upregulated in a rat model of chronic pancreatitis. Pancreas 2011;40:300-7.

Zhang, X-C. et al., Modulation of meningeal nociceptors mechanosensitivity by peripheral proteinase-activated receptor-2: the role of mast cells. Cephalalgia. Mar. 2008;28(3):276-84.

International Search Report and Written Opinion for PCT/US2019/026553, dated Aug. 1, 2019. 11 pages.

\* cited by examiner

SMALL MOLECULE MODULATORS OF PAR2 AND USES THEREOF

CROSS REFERENCE TO RELATED APPLICATIONS

This application is a U.S. 371 national phase entry of International Patent Application No. PCT/US2019/026553, filed Apr. 9, 2019, which claims priority to and the benefit of U.S. Provisional Application No. 62/654,969, filed Apr. 9, 2018, which are hereby incorporated by reference in their entireties.

STATEMENT REGARDING FEDERALLY SPONSORED RESEARCH OR DEVELOPMENT

This invention was made with government support under Grant Nos. R01 NS073664 and R56 NS098826, awarded by NIH. The government has certain rights in the invention.

FIELD OF THE INVENTION

This invention is in the field of medicinal pharmacology. In particular, the invention relates to a new class of small-molecules having a pyrazino-pyrimidine-dione (or related) structure which function as modulators (activators, inhibitors) of protease activated receptor type 2 ($PAR_2$), and their use as therapeutics for the treatment of conditions involving $PAR_2$ activity (e.g., asthma, chronic pain, cancer and/or vascular disorders).

INTRODUCTION

Chronic pain is a neurological disorder that impacts the lives of millions of Americans. Current treatments for chronic pain are limited by abuse potential and intolerable side effects. Endogenous proteases contribute to acute and chronic pain through the direct activation of the protease activated receptor-2 ($PAR_2$) G-protein coupled receptor (GPCR). $PAR_2$ is known to play an important role in chemical, inflammatory and cancer-induced pain but the possible efficacy of $PAR_2$ antagonists in these preclinical models has not been assessed due to lack of available tools or clinical candidate compounds. Moreover, activation of $PAR_2$ can lead to engagement of multiple signalling pathways yet agonists/antagonists with signalling pathway specific efficacy have not been explored as potential tools for understanding the role of $PAR_2$ signalling in nociception.

Asthma is a growing and potentially debilitating disease in the industrialized world. Available treatments for asthma have remained constant and novel approaches to therapies are needed. Cellular and animal studies have uncovered prominent roles for airway epithelial $PAR_2$ in detrimental inflammatory cytokine release and protective ecaisonoid release in response to allergic asthma. These apparently opposing responses can be targeted with novel compounds that individually or collectively modulate the multiple signalling pathways associated with allergen-induced $PAR_2$ activation.

Migraine pain is a major clinical problem. Almost 15 percent of the global population is affected by migraines during their lifetimes (see, e.g., Vos, T., et al., Lancet, 2012. 380(9859): p. 2163-96), and there are over 36 million migraine sufferers in the US alone. Even with this significant number of patients, treatments for migraine pain remains little more effective than over-the-counter analgesics. Part of the problem is that migraine etiology is complex and not well understood. Unlike common headaches, migraines have a specific presentation in which a prodrome, aura, and postdrome may occur with the migraine pain lasting between 4 and 72 hours. Hypersensitivity to light and sound, cutaneous allodynia, nausea, and other sensory-motor irregularities are also common symptoms of migraines. It is widely accepted that the trigeminal sensory system, including durally-projecting trigeminal ganglion (TG) nociceptors, is responsible for the pain associated with migraines (see, e.g., Bernstein, C. and R. Burstein, Journal of clinical neurology, 2012. 8(2): p. 89-99; Levy, D., Headache, 2010. 50(5): p. 909-16). However, it is not understood how the nociceptive afferents from the trigeminal system are activated/sensitized during a migraine attack or where any insults may occur that trigger a migraine attack. It is considered likely that deep cephalic tissues such as the meninges, or possibly the calvarial periosteum, are the tissues involved in nociception during a migraine attack and both have been studied as such in animal models of migraine.

Previous work in the migraine field has shown that degranulation of mast cells in the meninges can release serine proteases which in turn activate PARs and that this response is able to activate dural afferents projecting in the trigeminal nerve (see, e.g., Zhang, X. C. and D. Levy, Cephalalgia, 2008. 28(3): p. 276-84). Zhang and Levy used single-unit recording electrophysiology to monitor neurons in the trigeminal ganglia of anesthetized rats and applied SLIGRL, a non-specific peptide activator of $PAR_2$, to the dura of these animals. SLIGRL exposure resulted in activation and sensitization of TG neurons. This work potentially reveals an important neuro-immune relationship that can explain a wide variety of migraine etiologies since mast cell degranulation can result from cortical spreading depression (CSD), nitric oxide (NO) donors, calcitonin gene-related peptide (CGRP), and heightened stress, all of which are associated with migraine. However, the use of SLIGRL is problematic as it also activates MrgprC11, a receptor that is expressed in DRG and TG neurons and contributes to sensory neuron sensitization, with overlapping potency and efficacy to SLIGRL action at $PAR_2$ (see, e.g., Ramachandran, R. and M. D. Hollenberg, Br J Pharmacol, 2008.153 Suppl 1: p. S263-82; Ossovskaya, V. S. and N. W. Bunnett, Physiol Rev, 2004. 84(2): p. 579-621; Boitano S, et al., Br J Pharmacol 172: 4535-4545, 2015).

Accordingly, improved methods for treating conditions involving aberrant $PAR_2$ activity, including chronic pain, asthma and migraine, are needed.

SUMMARY OF THE INVENTION

Protease-activated receptor type 2 ($PAR_2$) is a G-protein-coupled receptor (GPCR) implicated in disease conditions including allergic asthma (Br J Pharmacol 2009; 158:1017-33), cancer (Scand J Gastroenterol 2008; 43:902-9) arthritis (Biol Chem 2008; 389:971-82), and chronic pain (Physiol Rev 2004; 84:579-621). $PAR_2$ can be activated in response to various exogenous and endogenous proteases (Br J Pharmacol 2008; 153(suppl 1):S263-282). Proteolytic cleavage of the N terminus results in exposure of a tethered ligand that activates the receptor to induce signaling (Physiol Rev 2004; 84:579-621). The primary method to study $PAR_2$ has been small peptides or peptidomimetics that mimic the naturally cleaved tethered ligand thus bypassing proteolytic cleavage of the N-terminal domain. This approach can be problematic, however, because this peptide sequence also activates mas-related G protein-coupled receptors (Mrgpr and GPCRs) that are specifically expressed in the sensory system and are involved in pain and itch signaling (Sci Signal 2011; 4:ra45). Although $PAR_2^{-/-}$ mice have been indispensable for elucidating the role of this receptor in normal physiology and pathology (Physiol Rev 2004; 84:579-621), a lack of suitable pharmacological tools have hindered full exploration of the role of this receptor in disease conditions, including chronic pain (Pharmacol Ther 2011; 130:248-82). Highly potent, efficacious, and specific agonists have been developed (J Med Chem 2011; 54:1308-13; J Biol Chem 2011; 286:19076-88; J Physiol 2007; 578:715-33) and used in experiments to explore the role of PAR2 in the development of a chronic pain state.

$PAR_2$ is thought to play an important role in inflammatory (Semin Thromb Hemost 2006; 32(suppl 1): 39-48; Physiol Rev 2004; 84:579-621; Nat Med 2001; 7:821-6 visceral (Gastroenterology 2011; 141:1864-74e1-3: J Clin Invest 2007; 117:636-47; Br J Pharmacol 2006; 148:54-60; PAIN 2014; 155:1328-38 Pancreas 2011; 40:300-7), and cancer-evoked (Mol Pain 2014; 10:28; J Neurosci 2012; 32:14178-83; PAIN 2010; 149: 263-72; Eur J Pain 2013; 18:326-37) pain based on studies using $PAR_2^{-/-}$ mice and/or antagonists suggesting an important role of $PAR_2$ in pathological pain. Hyperalgesic priming models have emerged as an important paradigm for probing plasticity associated with chronic pain in the nociceptive system (Trends Neurosci 2009; 32:611-18). It has been previously demonstrated that a single injection of interleukin-6 (IL-6) induces hyperalgesic priming and that this priming is dependent on plasticity in the peripheral and central nervous system (J Neurosci 2011; 31:6646-53; J Neurosci 2010; 30:15113-23; Mol Pain 2013; 9:12; Mol Pain 2014; 10:45). This is consistent with similar experiments in rats using inflammatory stimuli (Trends Neurosci 2009; 32:611-18). Importantly, $PAR_2^{-/-}$ mice fail to show nociceptive sensitization in many inflammatory pain models (Semin Thromb Hemost 2006; 32(suppl 1):39-48) and $PAR_2$ mediates alterations in dorsal root ganglion (DRG) BDNF levels (Mol Pain 2014; 10:28), a critical factor for hyperalgesic priming (Mol Pain 2013; 9:12; Mol Pain 2014; 10:45).

A central hypothesis for experiments conducted during the course of developing embodiments for the present invention was that $PAR_2$ plays a pivotal role in causing acute pain, promoting chronic pain, and in both promoting and controlling asthma symptoms, and that high affinity ligands of $PAR_2$ will represent a novel class of analgesics with utility in a number of chronic pain conditions and in the control of asthma. Thus, a primary objective of experiments conducted during the course of developing embodiments for the present invention was to develop novel and specific ligands to $PAR_2$, and to evaluate $PAR_2$ ligand efficacy as novel analgesics in preclinical pain and asthma models. Indeed, experiments were conducted that demonstrated 1) inhibition of $PAR_2$ response by novel antagonists C732 and C781, and 2) the ability of C781 in vivo in mice to block mechanical hypersensitivity (a pain measure) in response to a PAR2 agonist (2AT-LIGRL, also known as 2AT).

Accordingly, this invention relates to a new class of small-molecules having a pyrazino-pyrimidine-dione (or related) structure which function as modulators (activators, inhibitors) of $PAR_2$, and their use as therapeutics for the treatment of conditions involving $PAR_2$ activity (e.g., inflammatory disorders such as asthma and chronic pain).

In certain embodiments, the modulating compounds which function as activators or inhibitors of $PAR_2$ proteins are small molecules. For example, in some embodiments the present invention provides small molecule compounds encompassed within Formulas I, II, III, IV, V, VI, VII, VIII, IX, X, XI or XII:

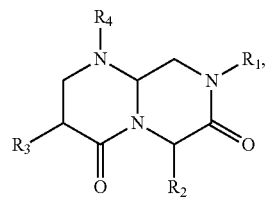
(Formula I)

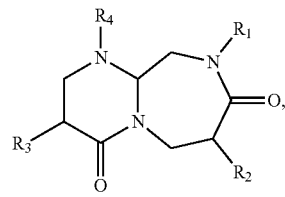
(Formula II)

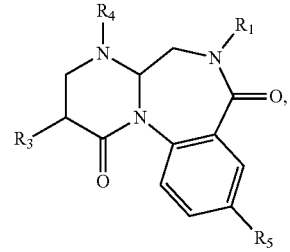
(Formula III)

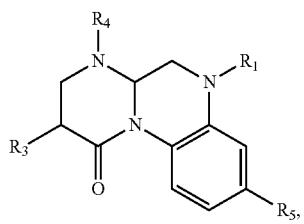
(Formula IV)

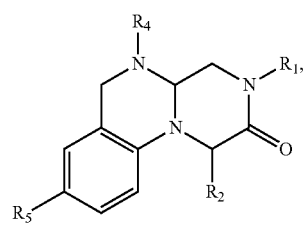
(Formula V)

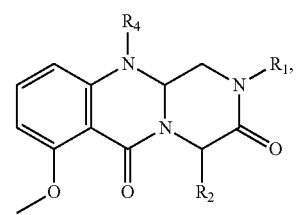
(Formula VI)

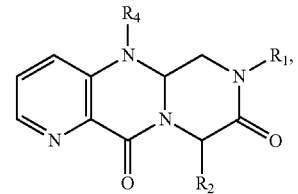
(Formula VII)

US 11,952,379 B2

-continued (Formula VIII)
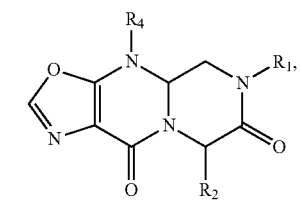

(Formula IX)
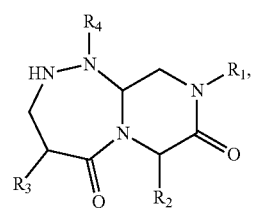

(Formula X)
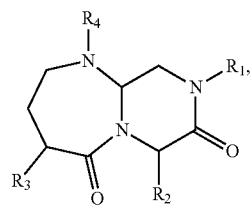

(Formula XI)
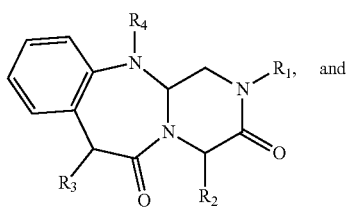 and (Formula XII)
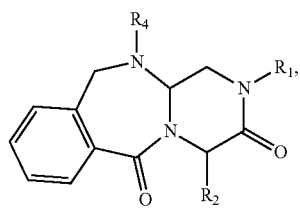

including pharmaceutically acceptable salts, solvates, and/or prodrugs thereof.

Formulas I, II, III, IV, V, VI, VII, VIII, IX, X, XI and XII are not limited to a particular chemical moiety for $R_1$, $R_2$, $R_3$, $R_4$, and $R_5$. In some embodiments, the particular chemical moiety for $R_1$, $R_2$, $R_3$, $R_4$, and $R_5$ independently include any chemical moiety that permits the resulting compound to function as an inhibitor of $PAR_2$ protein activity. In some embodiments, the particular chemical moiety for $R_1$, $R_2$, $R_3$, $R_4$, and $R_5$ independently include any chemical moiety that permits the resulting compound to function as an activator of $PAR_2$ protein activity.

Such compounds are not limited to a particular chemical moiety for $R_1$. In some embodiments, $R_1$ is selected from hydrogen,

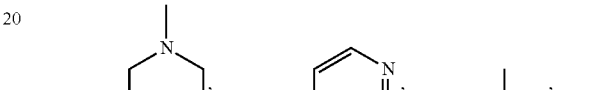

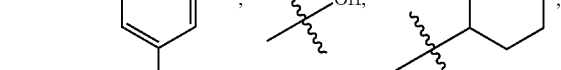

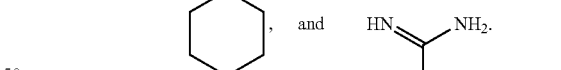

Such compounds are not limited to a particular chemical moiety for $R_2$. In some embodiments, $R_2$ is an amino acid selected from hydrogen,

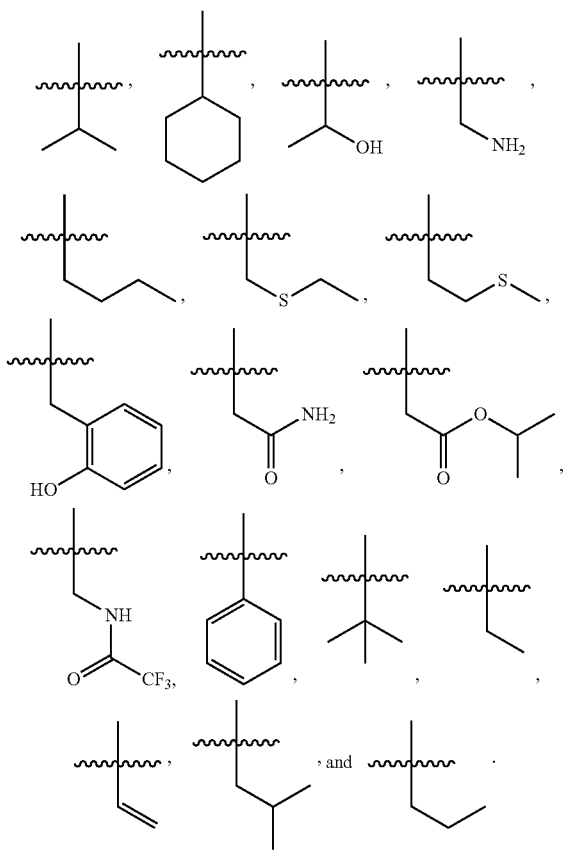
Such compounds are not limited to a particular chemical moiety for $R_3$. In some embodiments, $R_3$ is selected from hydrogen,
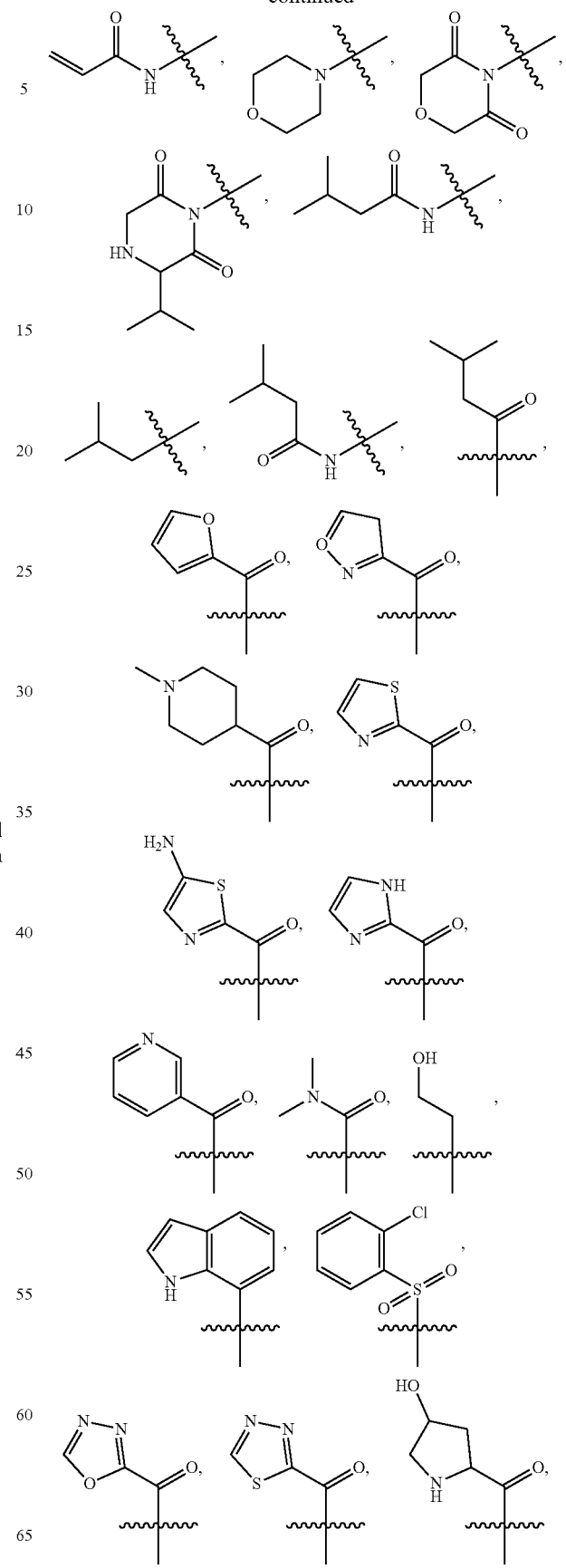

-continued

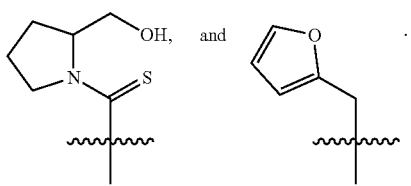

Such compounds are not limited to a particular chemical moiety for $R_4$. In some embodiments, R4 is selected from hydrogen,

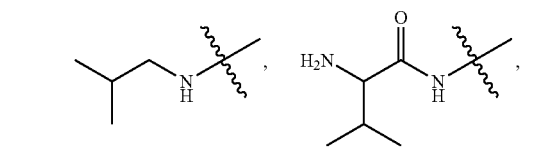
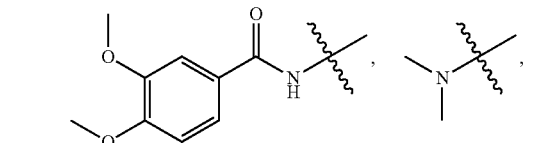
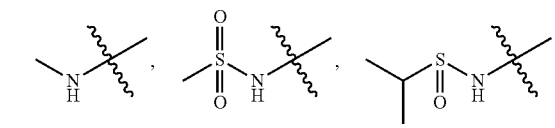
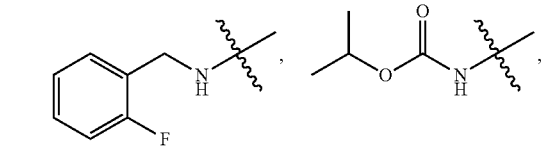
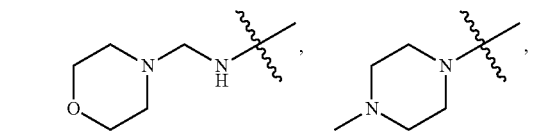
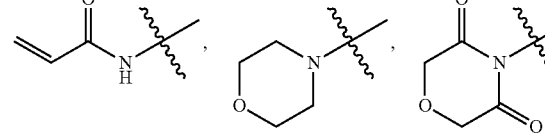
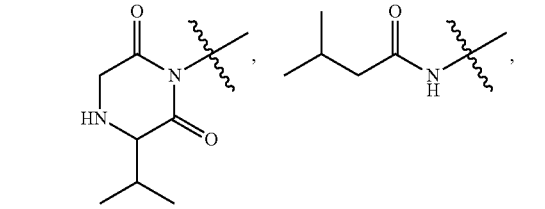
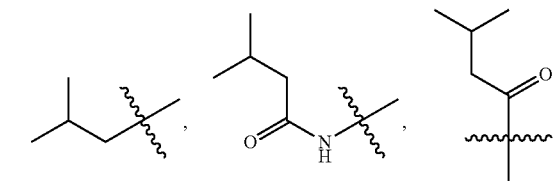

-continued

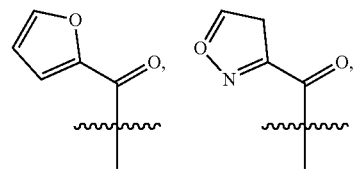
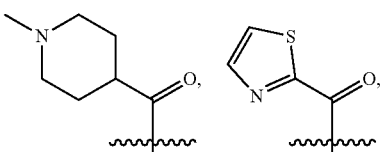
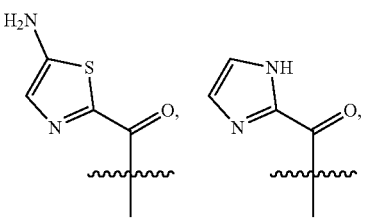
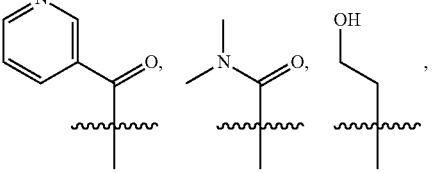
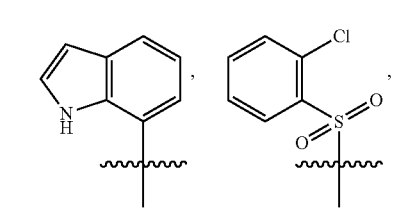
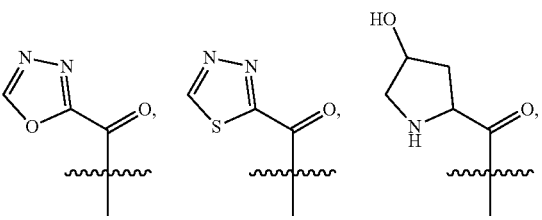
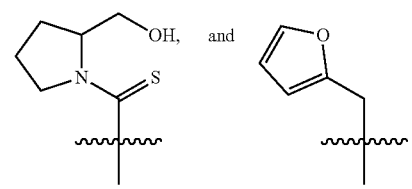

Such compounds are not limited to a particular chemical moiety for $R_5$. In some embodiments, R5 is either hydrogen or methyl.

In certain embodiments, the following compounds are provided as encompassed within Formulas I, II, III, IV, V, VI, VII, VIII, IX, X, XI or XII:

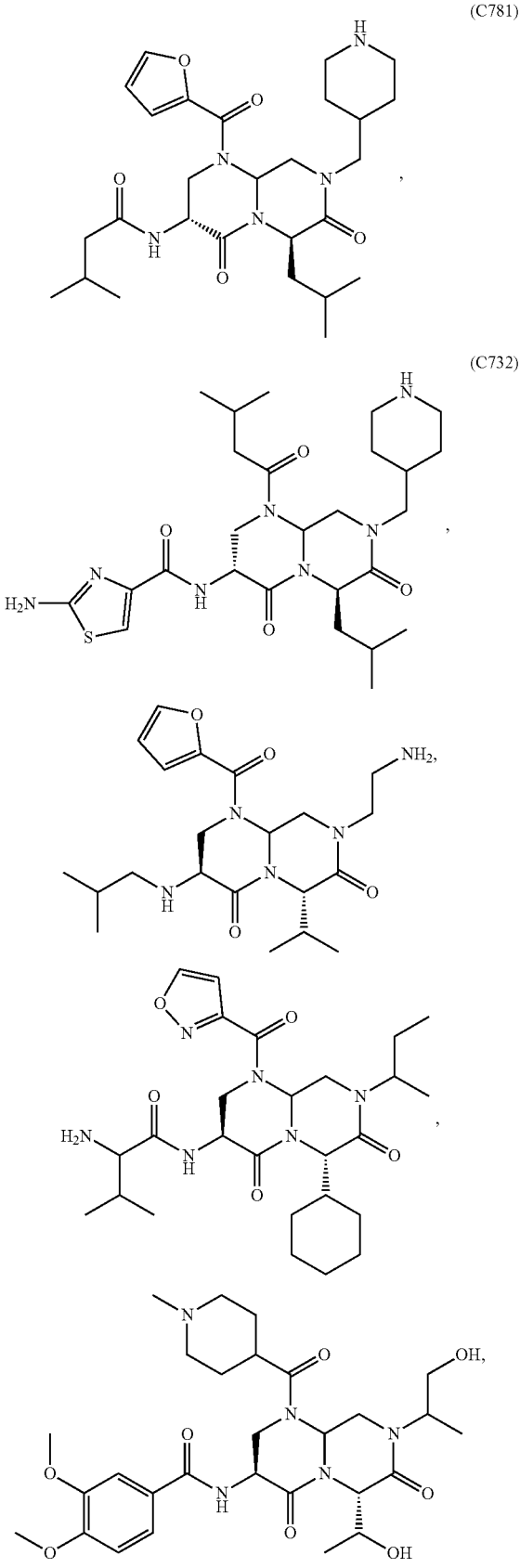
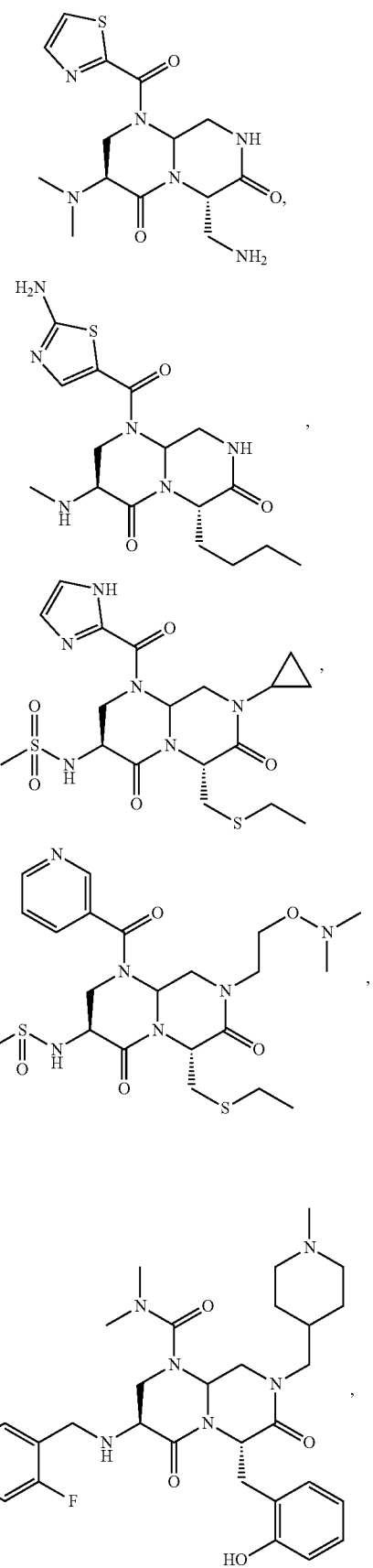

13
-continued
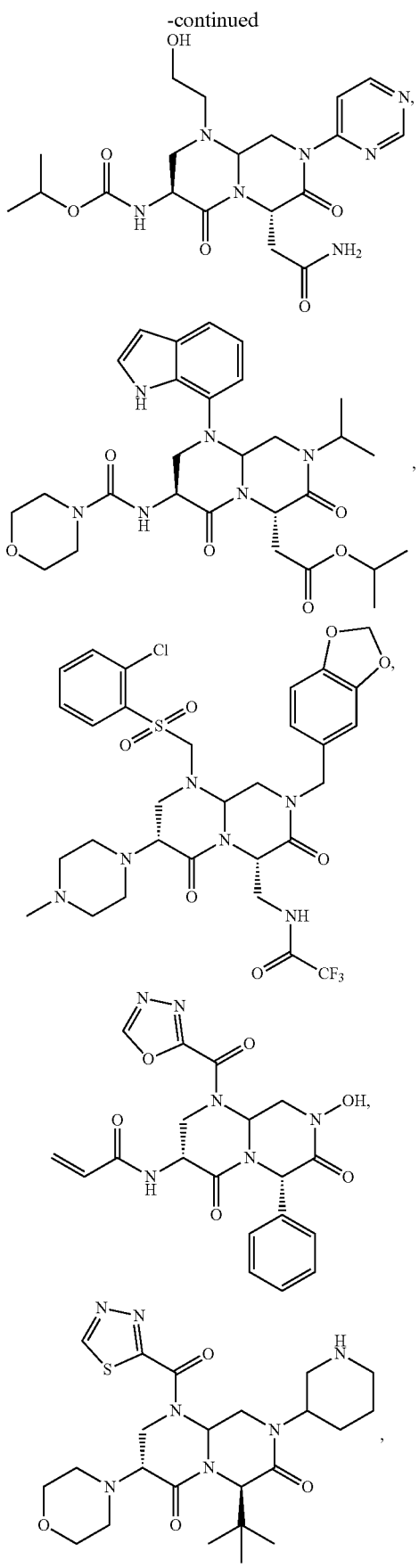
14
-continued
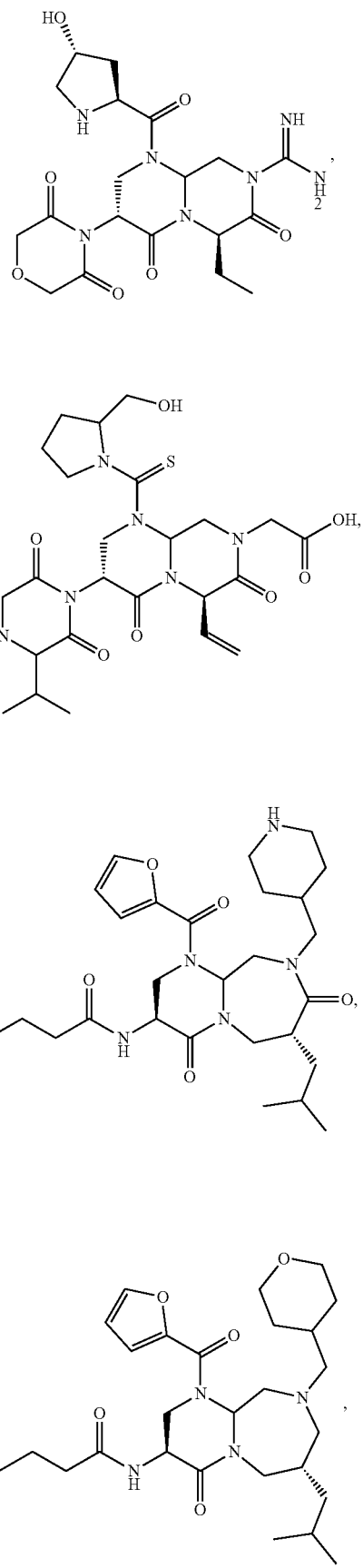

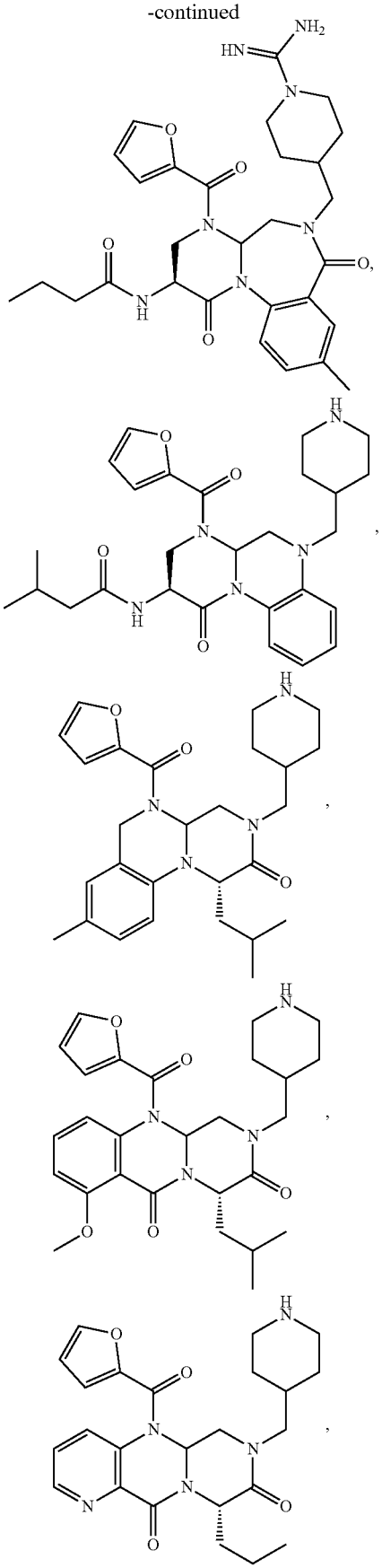
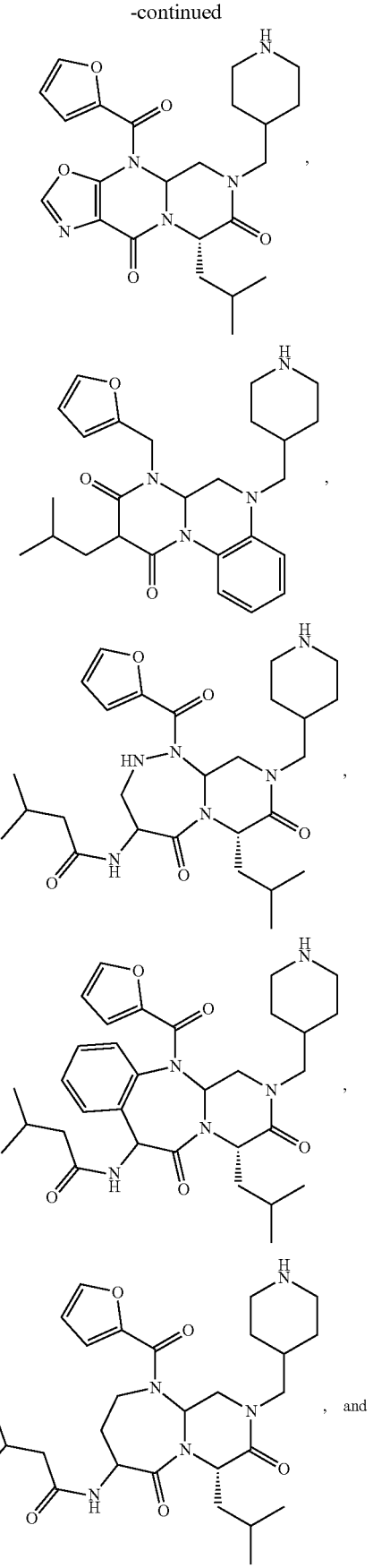

-continued

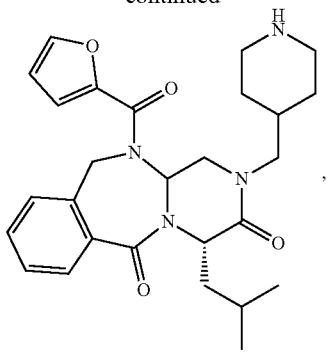

including pharmaceutically acceptable salts, solvates, and/or prodrugs thereof.

In certain embodiments, the present invention provides methods for modulating the activity of $PAR_2$ in a subject (e.g., human subject, non-human subject), comprising administering to the subject a $PAR_2$ modulating compound as described herein (e.g., a small molecule having a pyrazino-pyrimidine-dione structure (or related structure)) of the present invention. In some embodiments, the subject is experiencing aberrant $PAR_2$ activity. In some embodiments, the subject is at risk for experiencing aberrant $PAR_2$ activity. In some embodiments, the subject has or is at risk for developing an inflammatory condition (e.g., asthma) involving aberrant $PAR_2$ activity. In some embodiments, the subject has or is at risk for developing chronic pain involving aberrant $PAR_2$ activity.

In some embodiments, the inflammatory condition is one or more conditions selected from the group consisting of asthma, chronic pain, cancer, and a vascular disorder.

Regarding a treatment for asthma, the β-arrestin/MAPK signaling pathway leads to detrimental symptoms (inflammation, mucus overproduction) in asthma while the $Ca^{2+}$ signaling arm can provide beneficial effects (bronchial smooth muscle relaxation). Thus, the compounds of the present invention (e.g., C781) have the ideal biased agonist profile to work as a first in class allergic asthma drug.

Regarding a treatment for pain, while the $PAR_2$-dependent $Ca^{2+}$ signaling arm is important in acute pain responses, the β-arrestin/MAPK signaling arm also participates and likely participates in the transition from acute to chronic pain. Thus, the compounds of the present invention (e.g., C781) could serve as an acute pain antagonist that prevents the transition from acute to chronic pain (see, Example II and FIGS. 2 and 4).

In some embodiments, the methods further comprise administering to the subject one or more additional agents (e.g., anti-inflammatory agents, anti-cancer agents, pain-relieving agents). In some embodiments, the additional agent is an anti-inflammatory agent. In some embodiments, the anti-inflammatory agent is a non-steroidal anti-inflammatory drug. In some embodiments, anti-inflammatory agent is albuterol.

In certain embodiments, pharmaceutical compositions are provided. For example, in some embodiments, the present invention provides pharmaceutical compositions comprising a small molecule having a pyrazino-pyrimidine-dione structure (or related structure)) of the present invention and a pharmaceutically acceptable carrier.

In certain embodiments, the present invention provides kits comprising a pharmaceutical composition comprising a small molecule having a pyrazino-pyrimidine-dione structure (or related structure)) of the present invention and one or more additional agents (e.g., anti-inflammatory agents, anti-cancer agents, pain-relieving agents).

DETAILED DESCRIPTION OF THE INVENTION

Figure 1:
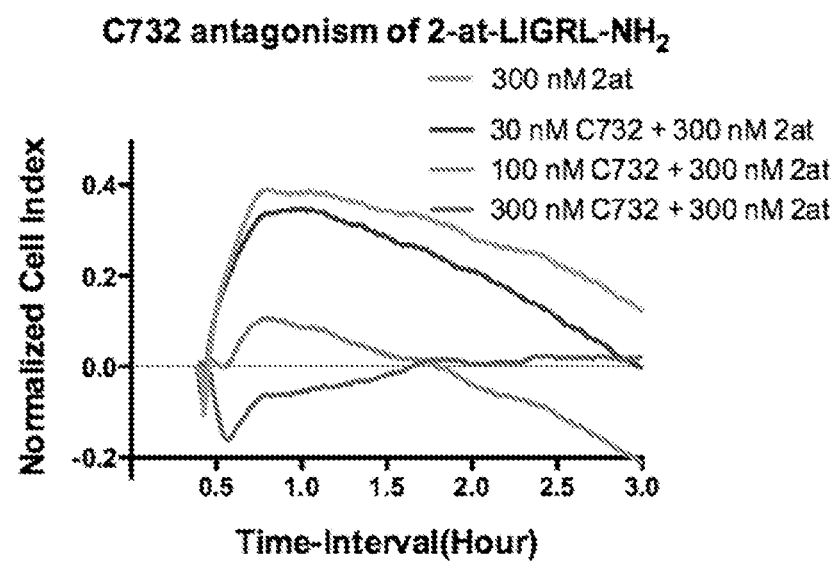
FIG. 1 shows inhibition of $PAR_2$ response by novel antagonists C732 and C781.
Figure 1:
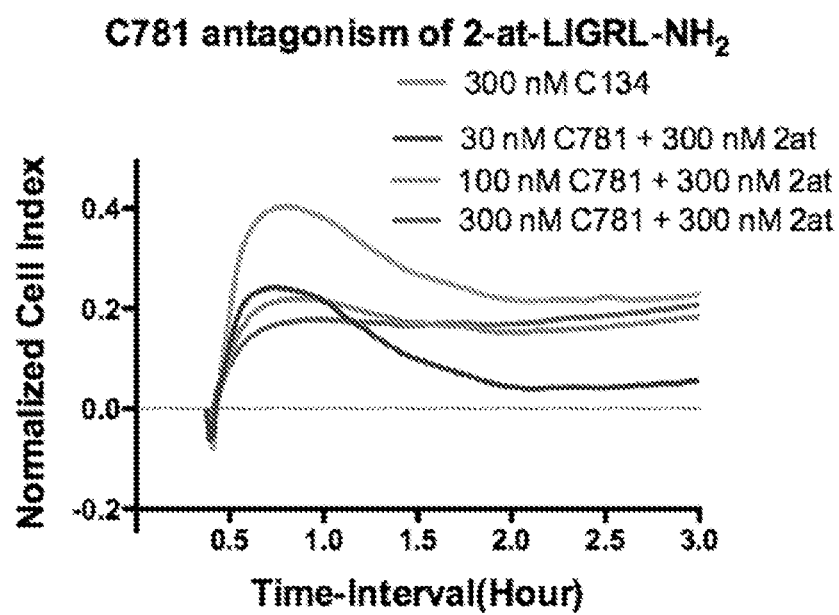

The protease-activated receptor-2 ($PAR_2$) is one of the four members of the family of GPCRs that are activated after proteolytic cleavage of their extracellular, amino terminus (Adams et al., Pharmacol. Ther. 130, 248-282; Ramachandran, R., et al., (2012) Nat. Rev. Drug Discov. 11, 69-86). The resulting 'tethered-peptide' sequence (ending with SLIGRL in the rodent receptor and SLIGKV in the human receptor) exposed after proteolytic cleavage activates $PAR_2$. A variety of potent and effective peptidomimetic agonists based upon the exposed tethered sequences have been developed to $PAR_2$ (Adams et al., Pharmacol. Ther. 130, 248-282; Boitano S, et al. (2014) PLoS ONE 9: e99140). These compounds have been very useful in understanding the consequences of $PAR_2$ activation across experimental models. However, the natural tethered agonist presentation for $PAR_2$, and its corresponding access to the $PAR_2$ binding pocket, has proved a difficult target for development of antagonists. Despite this difficulty, a number of $PAR_2$ antagonists have been proposed (Suen J Y, et al., (2012) Br J Pharmacol 165:1413-1423; Yau M K, et al., (2013) J Med Chem 56: 7477-7497). Further complicating the issue of drug development is the growing evidence for 'biased signalling' that can follow PAR2 agonism (Hollenberg, M. D., et al., 2014. 171(5): p. 1180-94) or antagonism (Goh, F. G., et al., British journal of pharmacology, 2009. 158(7): p. 1695-704; Suen, J. Y., et al., 2014. 171(17): p. 4112-24).

$PAR_2$ plays an important role in a variety of diseases linked to proteinase release from endogenous sources or exposure to exogenous proteinases (Ramachandran R, et al., (2012) Nat Rev Drug Discov 11: 69-86; Hollenberg, M. D., et al., 2014. 171(5): p. 1180-94). One consequence of $PAR_2$ activation in the peripheral nervous system is sensitization of neurons responsible for transmitting noxious information to the CNS. These nociceptive neurons express $PAR_2$, and $PAR_2$ activation on these neurons leads to enhanced signalling via a variety of channels including the capsaicin and noxious heat receptor, TRPV1 (Dai Y, et al., (2004) J Neurosci 24: 4293-4299). $PAR_2$ is responsible for proteinase sensitization of TRPV1 in vivo, leading to thermal hyperalgesia. $PAR_2$ null animals have deficits in pain sensitization in a variety of inflammatory pain models, and $PAR_2$ activation is sufficient to induce a transition to a chronic pain state, making this receptor an important target for drug development for pathological pain (Vergnolle N (2009) Pharmacol Ther 123: 292-309; Bao Y, et al., 2014 Expert Opin Ther Targets 18: 15-27; Tillu D V, et al. (2015) Pain 156: 859-867). Additionally, a broad variety of preclinical and clinical findings link exogenous proteinases, and more specifically $PAR_2$, to asthma (Reed C E, Kita H (2004) J Allergy Clin Immunol 114: 997-1008, quiz 1009; Vergnolle N (2009) Pharmacol Ther 123: 292-309; Jacquet A (2011) Clin Exp Allergy 41: 305-311; Snelgrove R J, et al., (2014) J Allergy Clin Immunol 134: 583-592). While there is a strong rationale for $PAR_2$ antagonist drug discovery for these indications, few $PAR_2$ antagonists have been described and even fewer have been demonstrated to exhibit efficacy in pre-clinical disease models (Yau, M. K., et al., J Med Chem, 2013. 56(19): p. 7477-97).

The present invention provides a new class of small-molecules having a pyrazino-pyrimidine-dione (or related) structure capable of modulating (e.g., activating, inhibiting) $PAR_2$ activity. Indeed, experiments were conducted that demonstrated 1) inhibition of $PAR_2$ response by novel antagonists C732 and C781, and 2) the ability of C781 in vivo in mice to block mechanical hypersensitivity (a pain measure) in response to a PAR2 agonist (2AT-LIGRL, also known as 2AT).

Accordingly, the invention relates to a new class of small-molecules having a pyrazino-pyrimidine-dione (or related) structure which function as modulators (activators, inhibitors) of protease activated receptor type 2 ($PAR_2$), and their use as therapeutics for the treatment of conditions involving $PAR_2$ activity (e.g., inflammatory disorders such as asthma and chronic pain).

In certain embodiments, the present invention provides modulating compounds which function as activators and inhibitors of $PAR_2$ proteins. In some embodiments the present invention provides small molecule compounds encompassed within Formulas I, II, III, IV, V, VI, VII, VIII, IX, X, XI or XII:

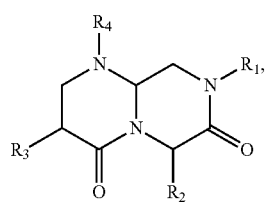
(Formula I)

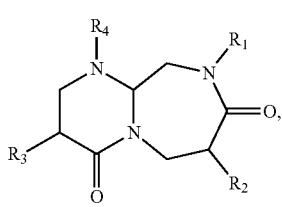
(Formula II)

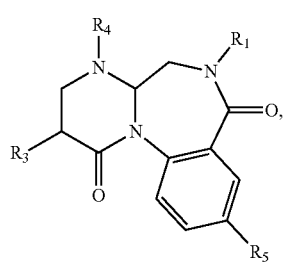
(Formula III)

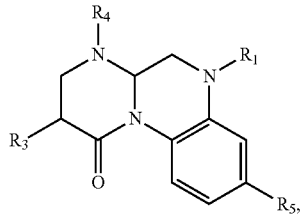
(Formula IV)

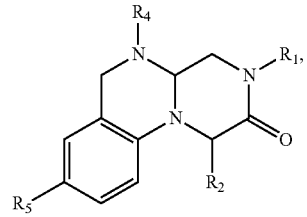
(Formula V)

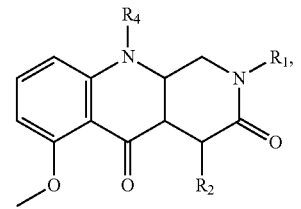
(Formula VI)

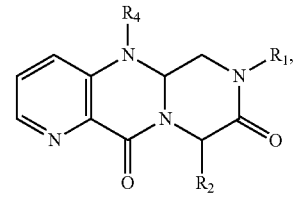
(Formula VII)

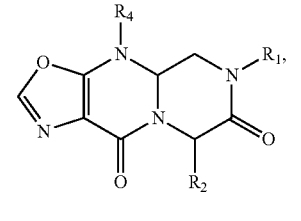
(Formula VIII)

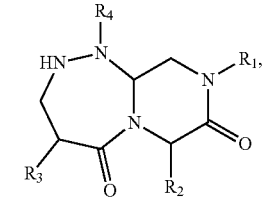
(Formula IX)

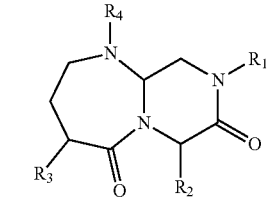
(Formula X)

-continued (Formula XII)

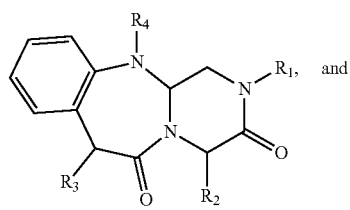

(Formula XII)

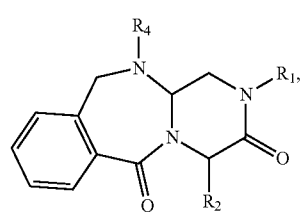

including pharmaceutically acceptable salts, solvates, and/or prodrugs thereof.

Formulas I, II, III, IV, V, VI, VII, VIII, IX, X, XI and XII are not limited to a particular chemical moiety for $R_1$, $R_2$, $R_3$, $R_4$, and $R_5$. In some embodiments, the particular chemical moiety for $R_1$, $R_2$, $R_3$, $R_4$, and $R_5$ independently include any chemical moiety that permits the resulting compound to function as an inhibitor of $PAR_2$ protein activity. In some embodiments, the particular chemical moiety for $R_1$, $R_2$, $R_3$, $R_4$, and $R_5$ independently include any chemical moiety that permits the resulting compound to function as an activator of $PAR_2$ protein activity.

Such compounds are not limited to a particular chemical moiety for $R_1$. In some embodiments, $R_1$ is selected from hydrogen, Such compounds are not limited to a particular chemical moiety for $R_2$. In some embodiments, $R_2$ is an amino acid selected from hydrogen,

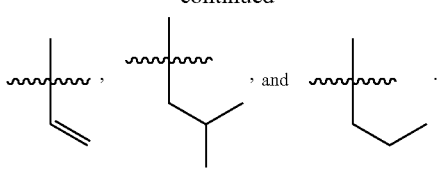
Such compounds are not limited to a particular chemical moiety for $R_3$. In some embodiments, $R_3$ is selected from hydrogen,
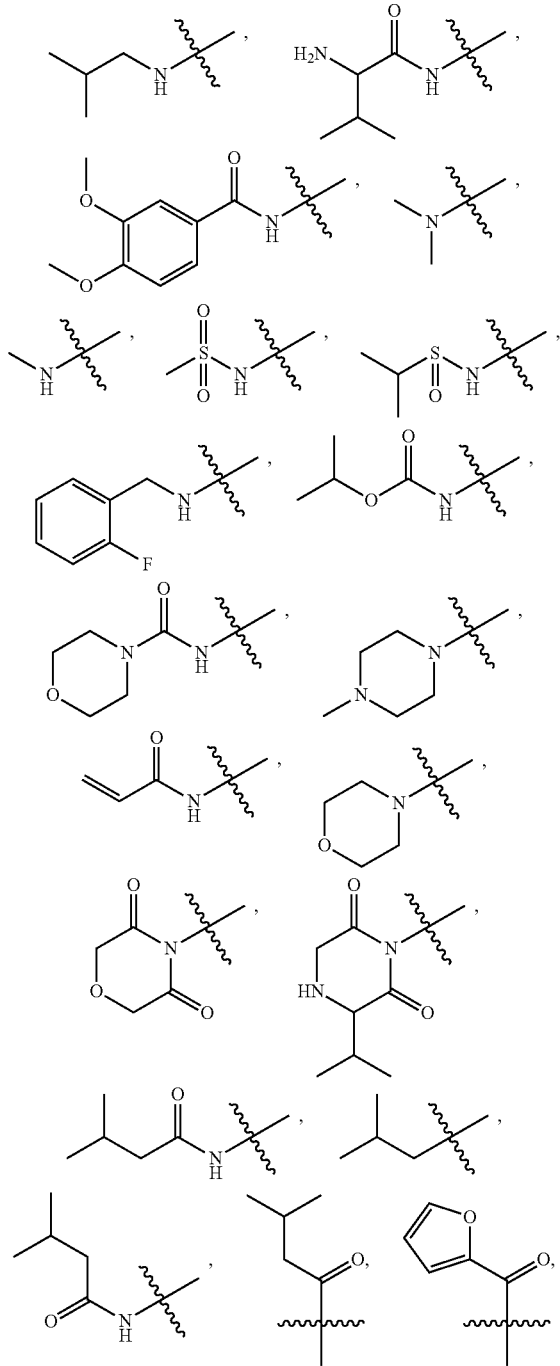
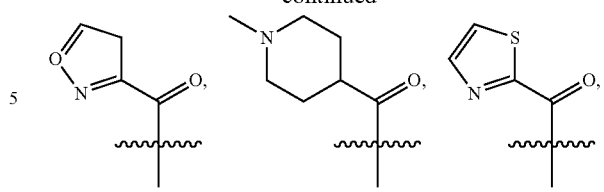
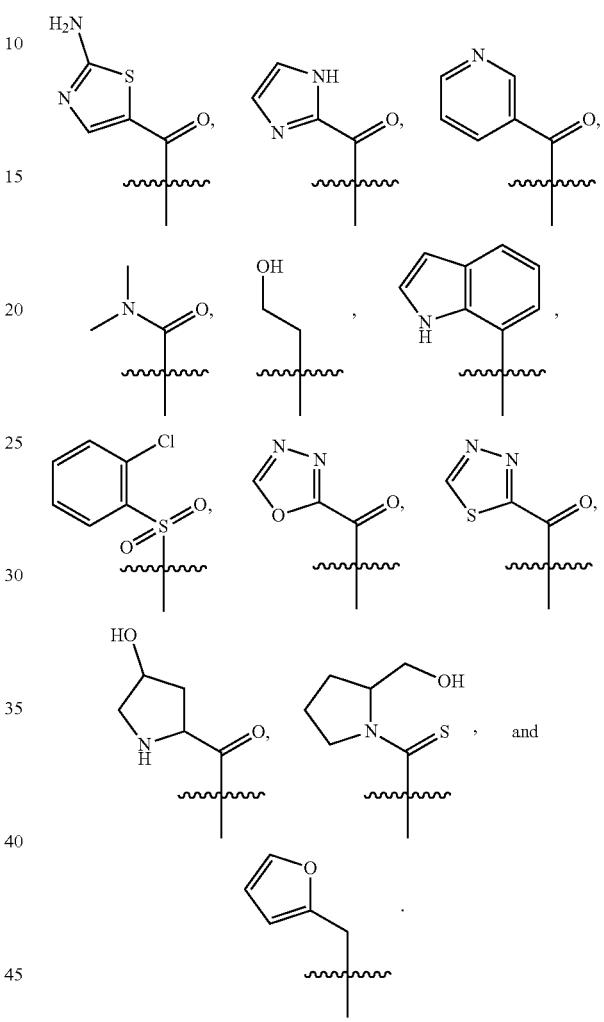
Such compounds are not limited to a particular chemical moiety for $R_4$. In some embodiments, R4 is selected from hydrogen,
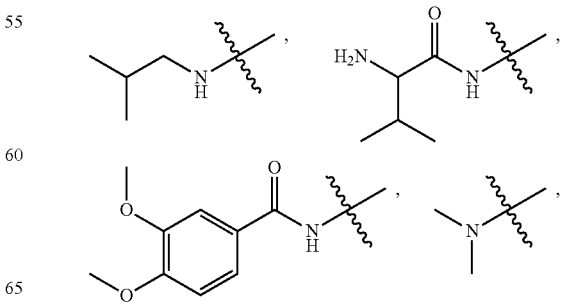

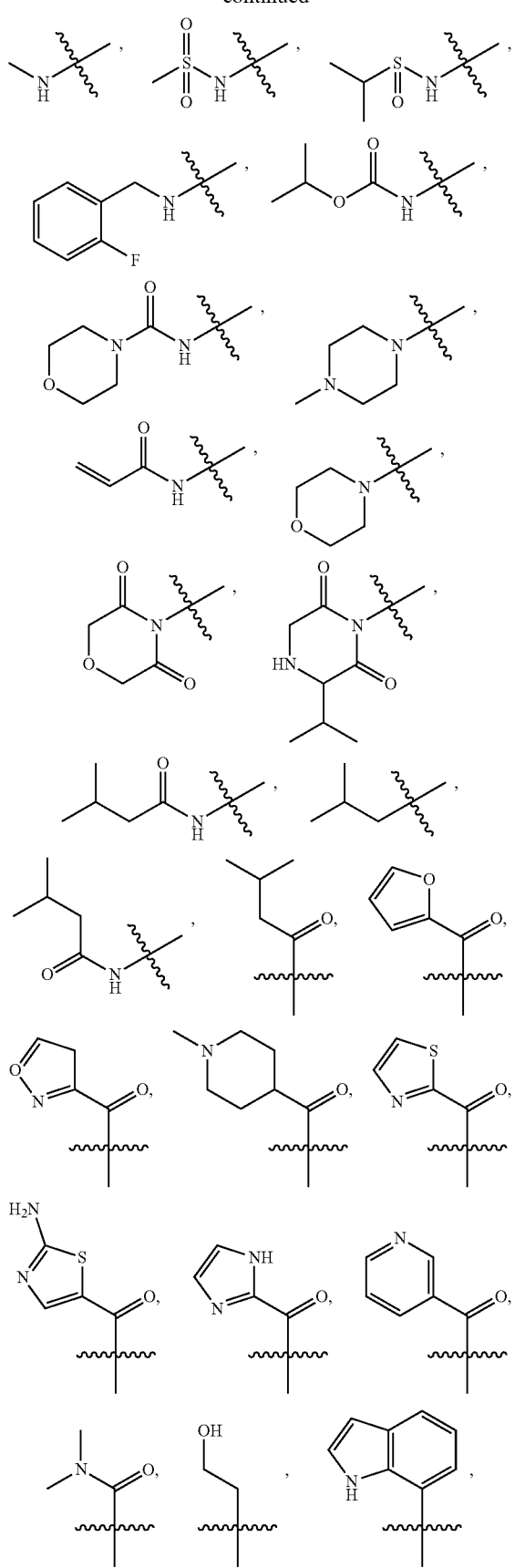
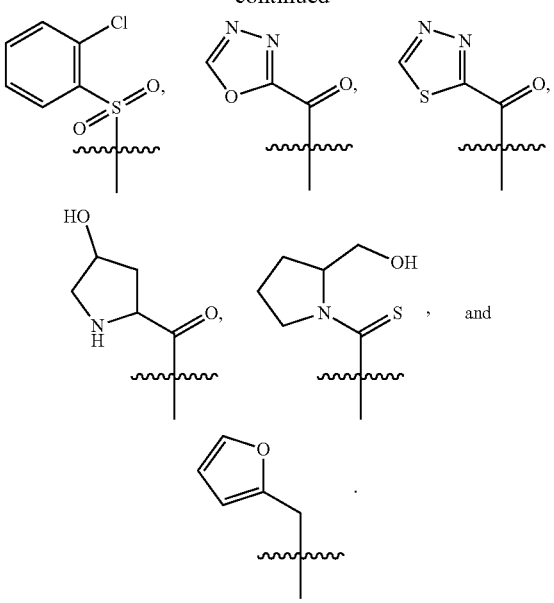
Such compounds are not limited to a particular chemical moiety for $R_5$. In some embodiments, R5 is either hydrogen or methyl.
In certain embodiments, the following compounds are provided as encompassed within Formulas I, II, III, IV, V, VI, VII, VIII, IX, X, XI or XII:
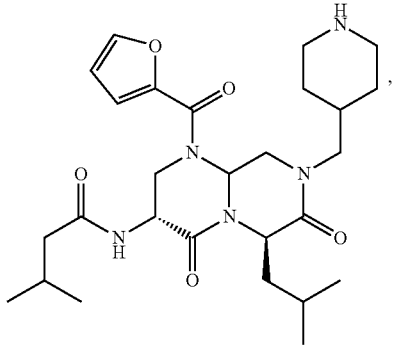
(C781)
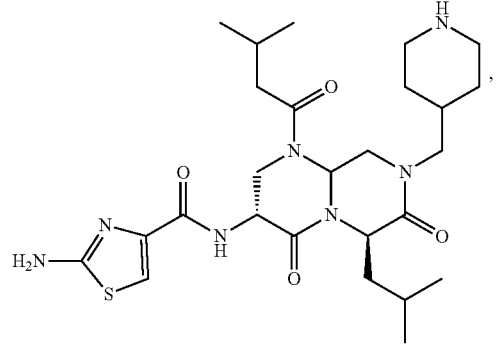
(C732)

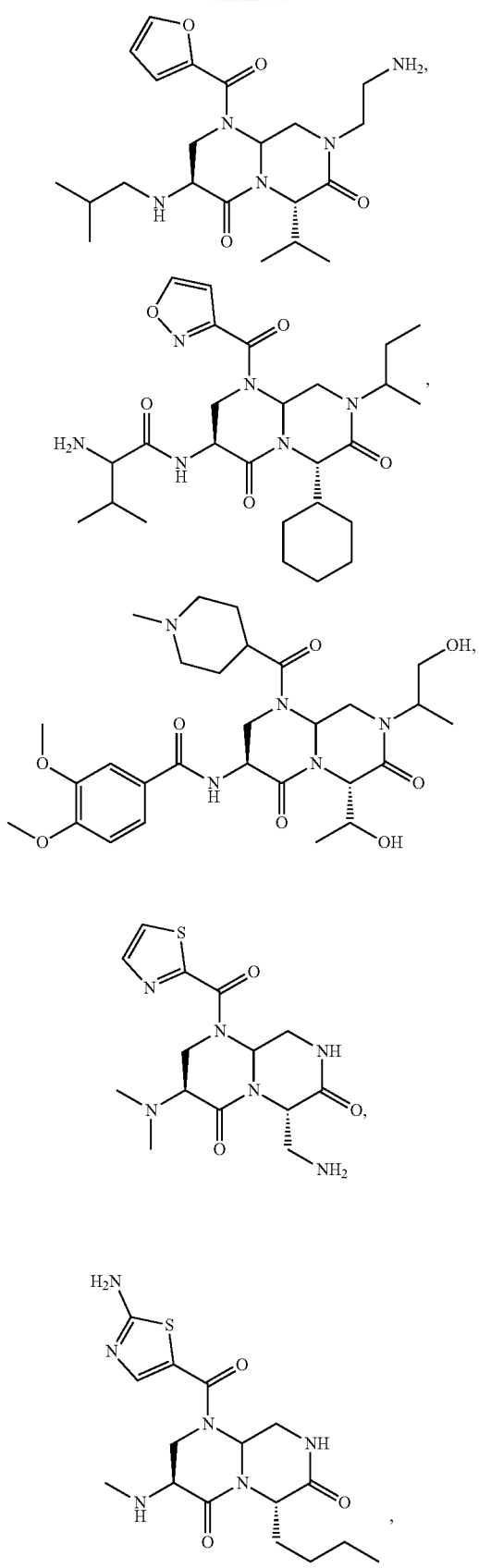
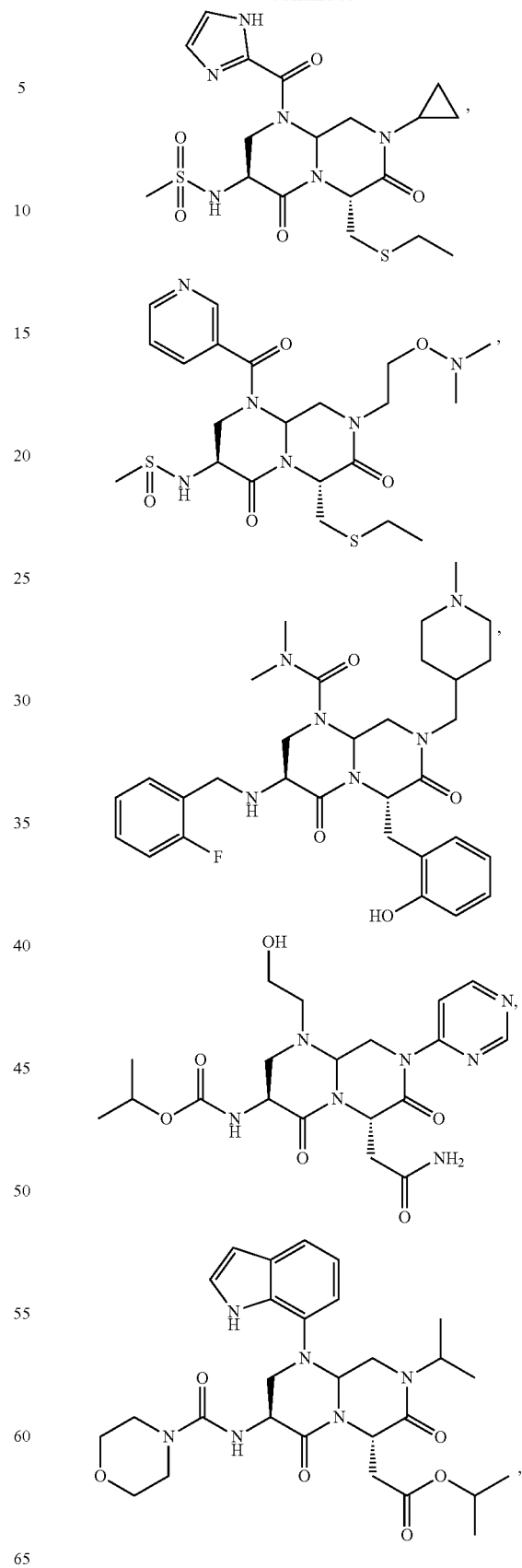

29
-continued
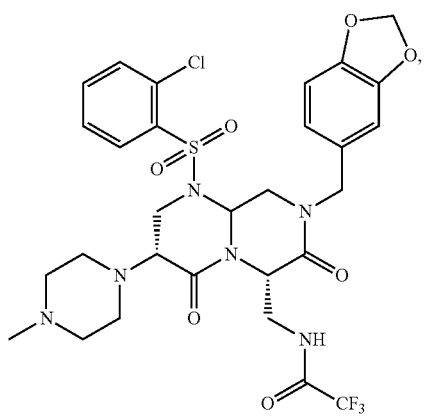
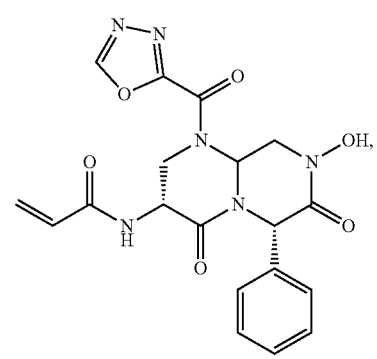
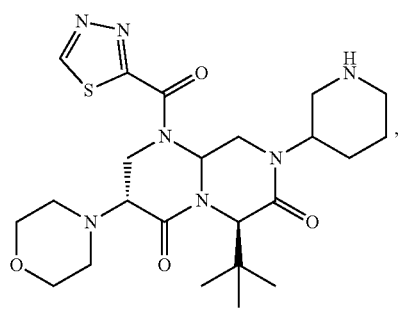
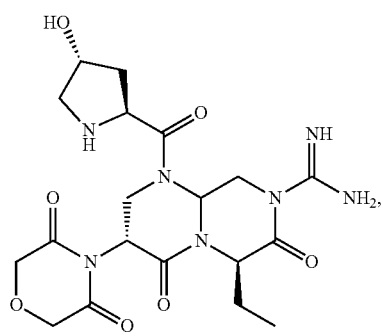
30
-continued
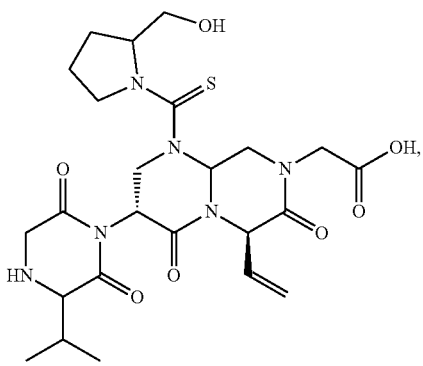
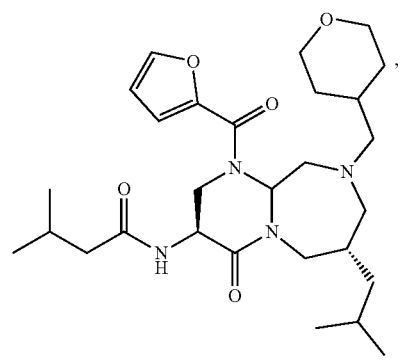
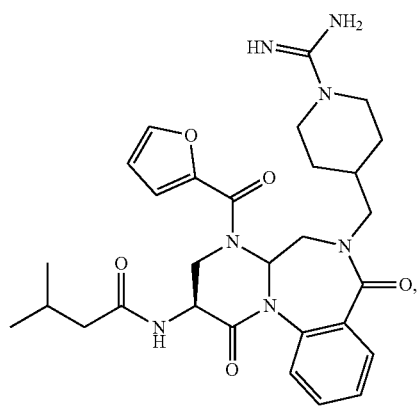

31
-continued
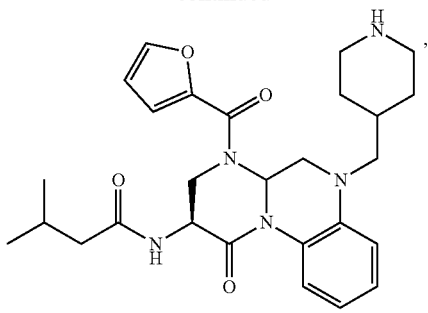
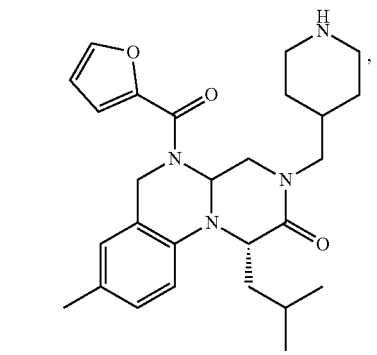
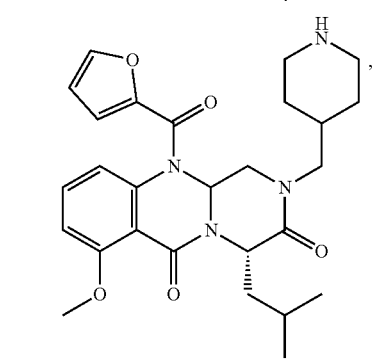
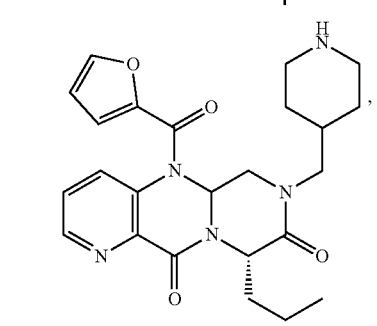
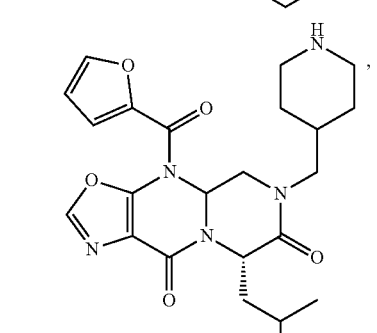
32
-continued
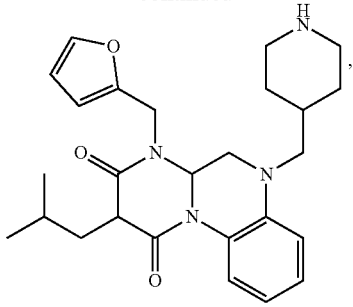
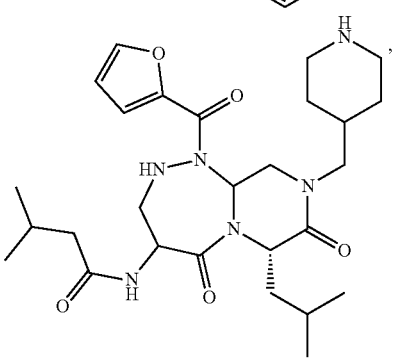
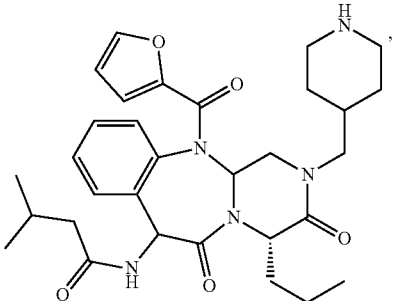
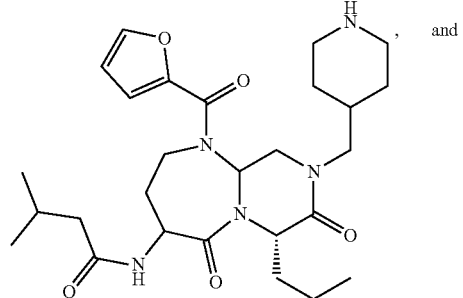, and
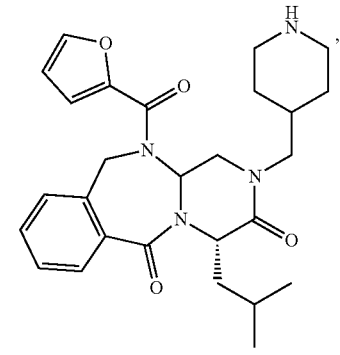

including pharmaceutically acceptable salts, solvates, and/or prodrugs thereof.

Indeed, an important aspect of the present invention is that the compositions of the present invention are useful in treating conditions characterized with aberrant $PAR_2$ activity. For example, in some embodiments, compositions comprising $PAR_2$ modulating compounds are used to treat inflammatory conditions through antagonizing $PAR_2$ activity. Such conditions include, but are not limited to, asthma, chronic pain, cancer and/or vascular disorders. In some embodiments, the compositions and methods of the present invention are used to treat cells, tissues, organs, or pathological conditions and/or disease states in an animal (e.g., a mammalian patient including, but not limited to, humans and veterinary animals) having aberrant PAR2 activity. In this regard, various diseases and pathologies are amenable to treatment or prophylaxis using the present methods and compositions. A non-limiting exemplary list of these diseases and conditions includes, but is not limited to, cancers having aberrant activity, inflammatory conditions having aberrant $PAR_2$ activity, asthma, chronic pain, and/or vascular disorders having aberrant $PAR_2$ activity.

Some embodiments of the present invention provide methods for administering an effective amount of a $PAR_2$ modulating compound of the invention and at least one additional therapeutic agent (including, but not limited to, pain relieving agents, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

A number of suitable anti-inflammatory agents are contemplated for use in the methods of the present invention. Examples include steroidal anti-inflammatory agents (e.g., albuterol), and non-steroidal anti-inflammatory agents.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics;

antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In some embodiments, the pain relieving agents include, but are not limited to, analgesic drugs and respective antagonists. Examples of analgesic drugs include, but are not limited to, paracetamol and Non-steroidal anti-inflammatory drugs (NSAIDs), COX-2 inhibitors, opiates and morphonimimetics, and specific analgesic agents.

Examples of NSAIDs include, but are not limited to, salicylates (e.g., Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate, Salicylamide), arylalkanoic acids (e.g., Diclofenac, Aceclofenac, Acemethacin, Alclofenac, Bromfenac, Etodolac, Indometacin, Nabumetone, Oxametacin, Proglumetacin, Sulindac, Tolmetin), 2-arylpropionic acids (profens) (e.g., Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids (fenamic acids) (e.g., Mefenamic acid, Flufenamic acid, Meclofenamic acid, Tolfenamic acid), pyrazolidine derivatives (e.g., Phenylbutazone, Ampyrone, Azapropazone, Clofezone, Kebuzone, Metamizole, Mofebutazone, Oxyphenbutazone, Phenazone, Sulfinpyrazone), oxicams (e.g., Piroxicam, Droxicam, Lornoxicam, Meloxicam, Tenoxicam), sulphonanilides (e.g., nimesulide), licofelone, and omega-3 fatty acids.

Examples of COX-2 inhibitors include, but are not limited to Celecoxib, Etoricoxib, Lumiracoxib, Parecoxib, Rofecoxib, Valdecoxib.

Examples of opiates include, but are not limited to, natural opiates (e.g., alkaloids contained in the resin of the opium poppy including morphine, codeine and thebaine), semi-synthetic opiates (e.g., created from the natural opioids, such as hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fully synthetic opioids (e.g., such as fentanyl, pethidine, Oxycodone, Oxymorphone, methadone, tramadol, Butorphanol, Levorphanol, and propoxyphene), and endogenous opioid peptides (e.g., produced naturally in the body, such as endorphins, enkephalins, dynorphins, and endomorphins).

Examples of analgesics include, but are not limited to, tricyclic antidepressants (e.g., amitriptyline, carbamazepine, gabapentin, and pregabalin), Tetrahydrocannabinol, ketamine, clonidine, $α_2$-adrenoreceptor agonists, mexiletine, Orphenadrine, cyclobenzaprine, scopolamine, atropine, gabapentin, first-generation antidepressants and other drugs possessing anticholinergic and/or antispasmodic.

In some embodiments, pain-relieving agents include anesthetic drugs. Examples of anesthetic drugs include, but are not limited to, local anesthetics (e.g., procaine, amethocaine, cocaine, lidocaine, prilocaine, bupivacaine, levobupivacaine, ropivacaine, dibucaine), inhaled anesthetics (e.g., Desflurane, Enflurane, Halothane, Isoflurane, Nitrous oxide, Sevoflurane, Xenon), intravenous anesthetics (e.g., Barbiturates (e.g., amobarbital (Amytal), pentobarbital (Nembutal), secobarbital (Seconal), Phenobarbital, Methohexital, Thiopental, Methylphenobarbital, Metharbital, Barbexaclone)), Benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), Etomidate, Ketamine, Propofol).

In some embodiments, pain-relieving agents include anticonvulsant drugs. Examples of anticonvulsant drugs include, but are not limited to, aldehydes (e.g., paraldehyde), aromatic allylic alcohols (e.g., stiripentol), barbiturates (e.g., amobarbital (Amytal), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), bromides (e.g., potassium bromide), carbamates (e.g., felbamate), carboxamides (e.g., carbamazepine, oxcarbazepine), fatty acids (e.g., valproates (e.g., valproic acid, sodium valproate, and divalproex sodium), Vigabatrin, Progabide, Tiagabine), fructose derivatives (e.g., topiramate), gaba analogs (e.g., gabapentin, pregabalin), hydantoins (e.g., Ethotoin, Phenytoin, Mephenytoin, Fosphenytoin), Oxazolidinediones (e.g., paramethadione, trimethadione, ethadione), priopionates (e.g., primidone), pyrrolidines (e.g., brivaracetam, levetiracetam, seletracetam), succinimides (e.g., Ethosuximide, Phensuximide, Mesuximide), sulfonamides (e.g., Acetazolamide, Sulthiame, Methazolamide, Zonisamide), triazines (e.g., lamotrigine), ureas (e.g., pheneturide, phenacemide), and valproylamdies (amide derivatives of valproate) (e.g., valpromide, valnoctamide).

In some embodiments, pain-relieving agents include muscle relaxant drugs. Examples of muscle relaxant drugs include, but are not limited to, depolarizing muscle relaxants (e.g., Succinylcholine), short acting non-depolarizing muscle relaxants (e.g., Mivacurium, Rapacuronium), intermediate acting non-depolarizing muscle relaxants (e.g., Atracurium, Cisatracurium, Rocuronium, Vecuronium), and long acting non-depolarizing muscle relaxants (e.g., Alcuronium, Doxacurium, Gallamine, Metocurine, Pancuronium, Pipecuronium, d-Tubocurarine).

In some embodiments, a $PAR_2$ modulating compound of the invention and one or more additional agents (e.g., anti-inflammatory agents, anti-cancer agents, pain-relieving agents) are administered to an animal (e.g., a human patient) under one or more of the following conditions: at different periodicities, at different durations, at different concentrations, by different administration routes, etc. In some embodiments, the $PAR_2$ modulating compound is administered prior to the one or more additional agents (e.g., anti-inflammatory agents, anti-cancer agents, pain-relieving agents), e.g., 0.5, 1, 2, 3, 4, 5, 10, 12, or 18 hours, 1, 2, 3, 4, 5, or 6 days, or 1, 2, 3, or 4 weeks prior to the one or more additional agents (e.g., anti-inflammatory agents, anti-cancer agents, pain-relieving agents). In some embodiments, the $PAR_2$ modulating compound is administered after the one or more additional agents (e.g., anti-inflammatory agents, anti-cancer agents, pain-relieving agents), e.g., 0.5, 1, 2, 3, 4, 5, 10, 12, or 18 hours, 1, 2, 3, 4, 5, or 6 days, or 1, 2, 3, or 4 weeks after the administration of the additional agent. In some embodiments, the $PAR_2$ modulating compound and the additional agent are administered concurrently but on different schedules, e.g., the $PAR_2$ modulating compound is administered daily while the additional agent is administered once a week, once every two weeks, once every three weeks, or once every four weeks. In other embodiments, the $PAR_2$ modulating compound is administered once a week while the additional agent is administered daily, once a week, once every two weeks, once every three weeks, or once every four weeks.

Compositions within the scope of this invention include all compositions wherein the $PAR_2$ modulating compounds of the present invention are contained in an amount that is effective to achieve its intended purpose. While individual needs vary, determination of optimal ranges of effective amounts of each component is within the skill of the art. Typically, the $PAR_2$ modulating compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to activation or inhibition of $PAR_2$ activity. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the $PAR_2$ modulating compound. The unit dose may be administered one or more times daily as one or more tablets or capsules each containing from about 0.1 to about 10 mg, conveniently about 0.25 to 50 mg of the $PAR_2$ modulating compound or its solvates.

In a topical formulation, the $PAR_2$ modulating compound may be present at a concentration of about 0.01 to 100 mg per gram of carrier. In a one embodiment, the $PAR_2$ modulating compound is present at a concentration of about 0.07-1.0 mg/ml, for example, about 0.1-0.5 mg/ml, and in one embodiment, about 0.4 mg/ml.

In addition to administering the $PAR_2$ modulating compound as a raw chemical, the $PAR_2$ modulating compounds of the invention may be administered as part of a pharmaceutical preparation containing suitable pharmaceutically acceptable carriers comprising excipients and auxiliaries which facilitate processing of the $PAR_2$ modulating compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound, together with the excipient.

The pharmaceutical compositions of the invention may be administered to any patient that may experience the beneficial effects of the $PAR_2$ modulating compounds of the invention. Foremost among such patients are mammals, e.g., humans, although the invention is not intended to be so limited. Other patients include veterinary animals (cows, sheep, pigs, horses, dogs, cats and the like).

The $PAR_2$ modulating compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye-stuffs or pigments may be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one that includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

EXPERIMENTAL

Example I

FIG. 1 shows inhibition of $PAR_2$ response by novel antagonists C732 and C781. Experiments demonstrated that C732 fully limited the 2at-LIGR1-$NH_2$-induced response at 100-300 nM, whereas C781 was affective at 30-300 nM (see, FIG. 1).

Example II

Experiments were conducted to test C781 in vivo in mice for its ability to block mechanical hypersensitivity (a pain measure) in response to a PAR2 agonist (2AT-LIGRL, also known as 2AT). C781 was shown to be effective through both local, and systemic injection.

Figure 2:
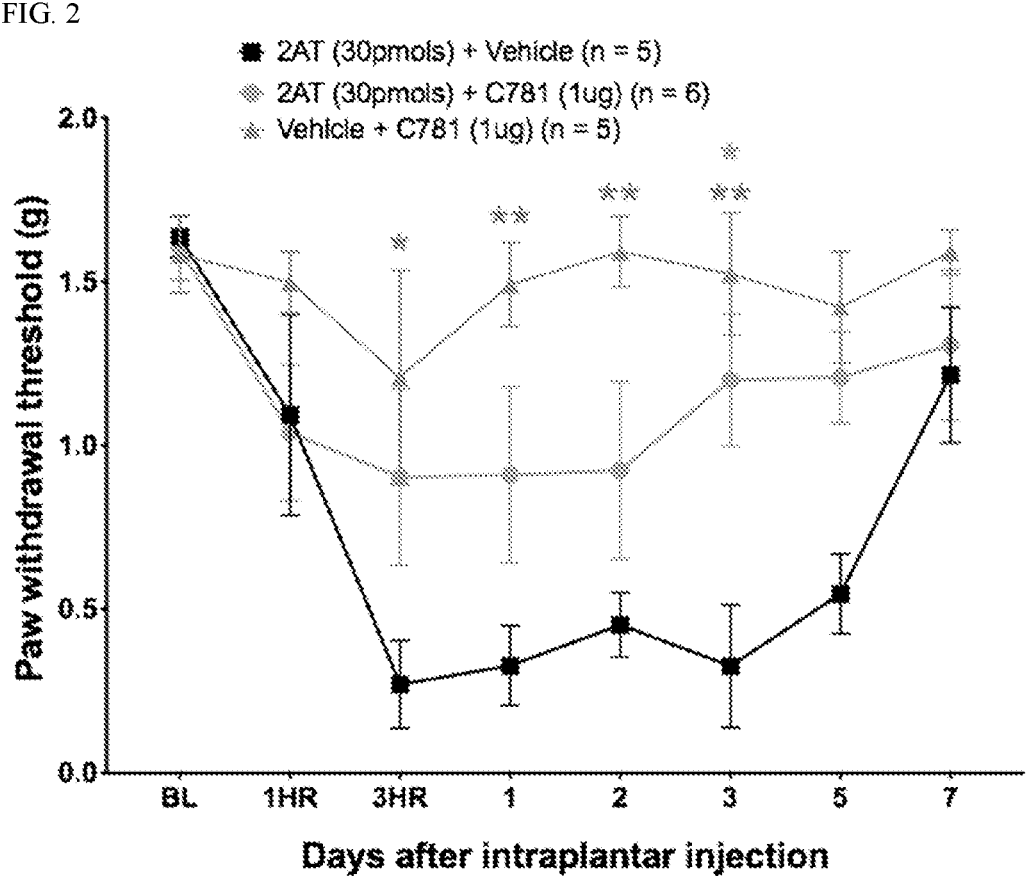
FIG. 2 shows that C781 blocked 2AT-evoked pain when given locally into the mouse hindpaw.

FIG. 2 shows that C781 limited pain-induced paw withdrawal response induced by the $PAR_2$ agonist 2-aminothiazol-LIGRL-$NH_2$ (2at). Animals were injected with 2at (black), 2at+C781(yellow), or C781 alone (green). 2at induced a rapid withdrawal response (lower numbers) indicative of pain. Locally administered C781 reduced the 2at response and had no effect when injected with vehicle alone.

Figure 3:
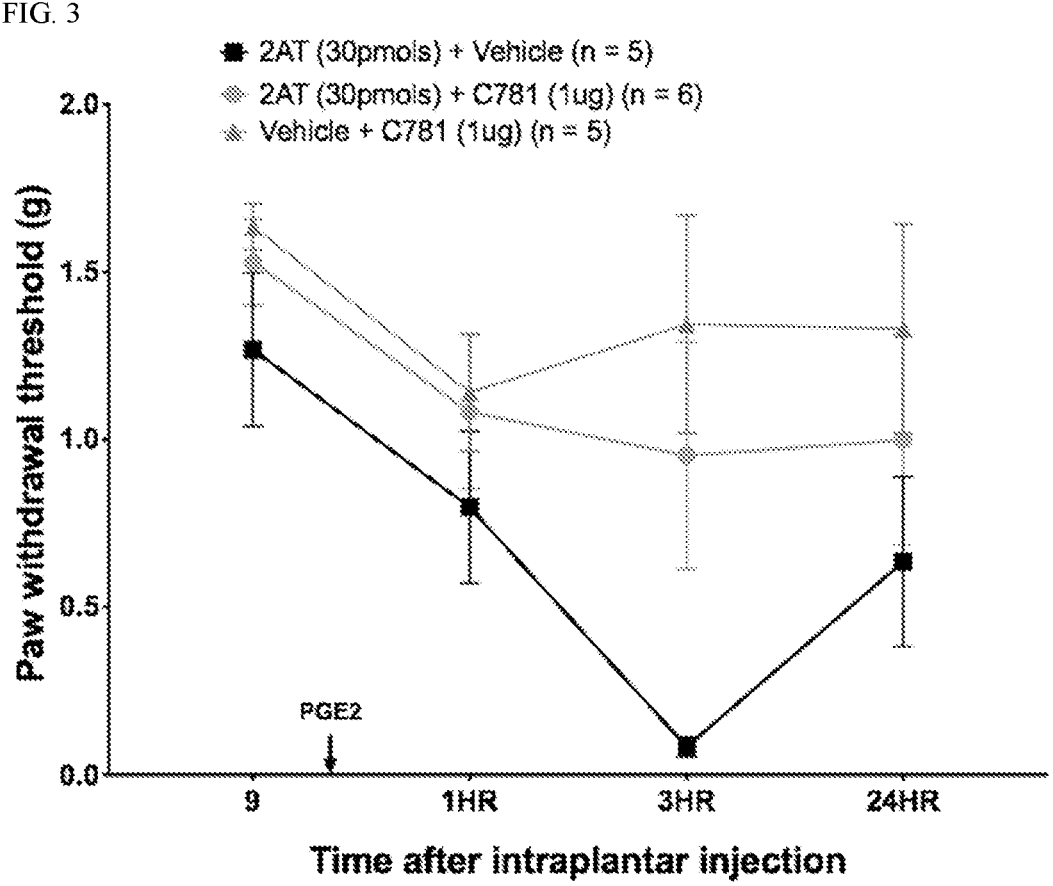
FIG. 3 shows that C781 blocked 2AT-evoked hyperalgesic priming when given locally into the mouse hindpaw.

FIG. 3 shows that C781 blocked 2AT-evoked hyperalgesic priming when given locally into the mouse hindpaw.

Figure 4:
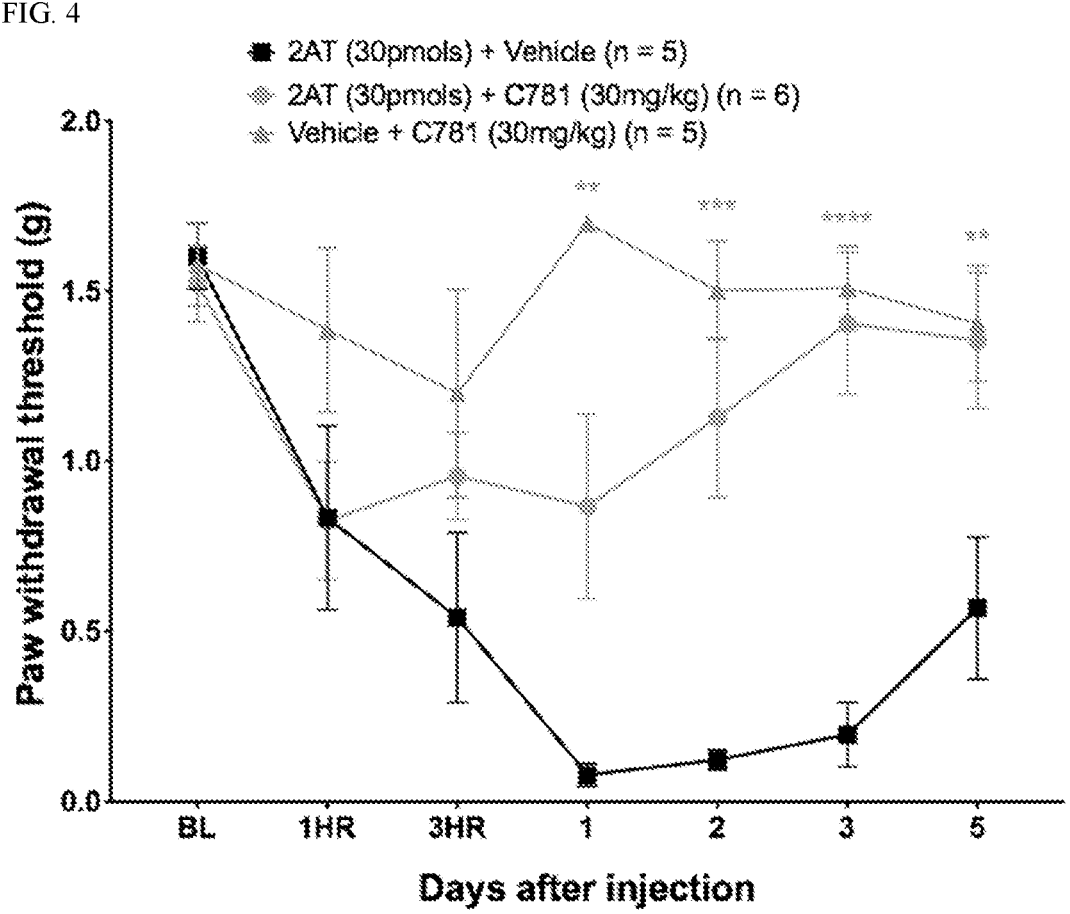
FIG. 4 shows that systemic application of C781 limits pain-induced paw withdrawal response following $PAR_2$ activation.

FIG. 4 shows that C781 blocked 2AT-evoked pain when given intraperitoneally 30 min prior to 2AT injection into the hindpaw. Animals were systemically treated with C781 or control and then local injected with 2at (black with control; yellow with C781) or with vehicle alone (green). Systemically administered C781 reduced the 2at response and had no effect on vehicle treatment. This is important because previous PAR$_2$ antagonists have not had systemic bioavailability and have only worked with very high doses via intravenous injection.

Figure 5:
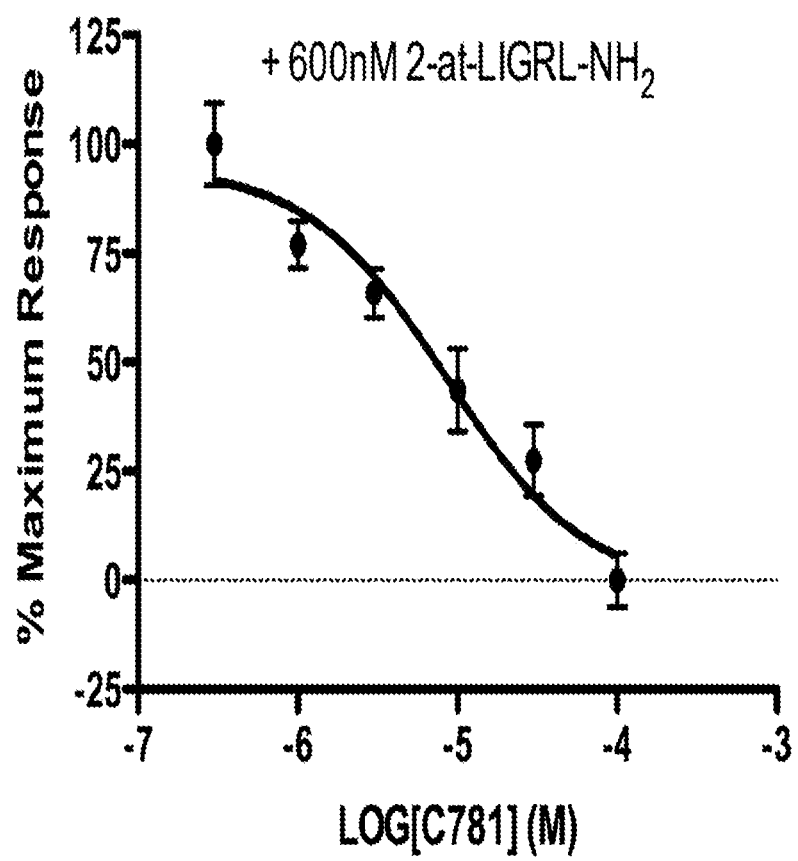
FIG. 5 shows that C781 prevented $PAR_2$-dependent MAPK signaling.

FIG. 5 shows that C781 prevented PAR$_2$-dependent MAPK signaling. Addition of 600 nM of the potent PAR$_2$ agonist 2at-LIGRL-NH$_2$ induced significant phosphorylation of MAPK (100% response). Treatment with C781 significantly reduced the response with an IC$_{50}$ of 8.5 µM (95% CI: 3.4 µM-21 µM).

Figure 6:
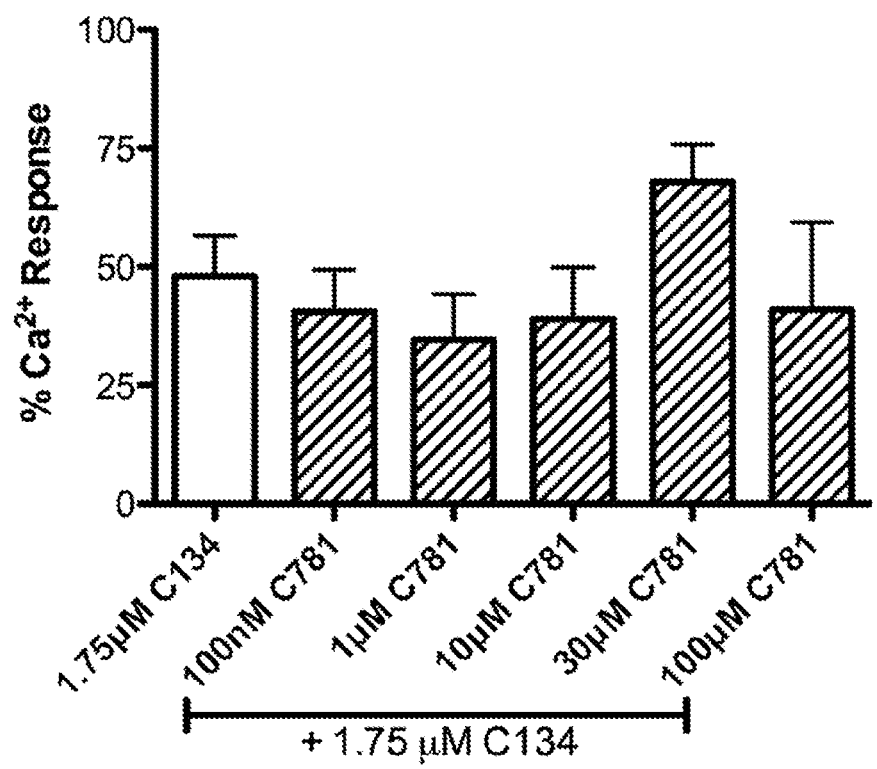
FIG. 6 shows that C781 has no effect on $PAR_2$-dependent $Ca^{2+}$ signaling.

FIG. 6 shows that C781 has no effect on PAR$_2$-dependent Ca$^{2+}$ signaling. Addition of 1.75 µM of the potent PAR$_2$ agonist 2at-LIGRL-NH$_2$ (C134) induced Ca$^{2+}$ signaling in 50% of the cells within the experiment. C781 has no significant effect on Ca' signaling when administered with C134.

Example III

Synthesis of Azabicycloalkane Compounds Formula I:

Chemical Materials:

N-α-Fmoc-protected amino acids, TCFH, DIC, and HOBt were purchased from SynPep (Dublin, CA) or from Novabiochem (San Diego, CA). Bromoacetal, 2-Chloro-chlorotrityl, and Wang resins were acquired from Rapp Polymere (Tubingen, Germany). For the Nα-Fmoc-protected amino acids, the following side chain protecting groups were used: Dap(N$^β$-Aloc). Reagent grade solvents, reagents, and acetonitrile for HPLC were acquired from VWR (West Chester, PA) or Aldrich-Sigma (Milwaukee, WI), and were used without further purification unless otherwise noted. Chemicals and reagents were obtained from Sigma-Aldrich or TCI. The solid-phase synthesis was performed in fritted syringes using a Domino manual synthesizer obtained from Torviq (Niles, MI).

General Synthesis:

All solution phase reactions were conducted under Ar atmosphere using oven-dried glassware. All chemicals were obtained from commercial sources and used without further purification. $^1$H NMR spectra were recorded on a Bruker-DRX-300 MHz instrument with chemical shifts reported relative to TMS (0.0 ppm) and residual DMSO (2.50 ppm). Proton-decoupled $^{13}$C NMR spectra were referenced to CDCl$_4$ (77.0 ppm) as well as DMSO (39.51 ppm). Low resolution mass spectra were obtained on AGILENT (HP) MDS 1100 using AP-ESI. High resolution mass spectra (HRMS) were recorded on a JEOL HX110A instrument.

General Synthetic Scheme A:

Scheme A. Solid-phase synthesis of compounds Formula I.

Bromoacetal resin

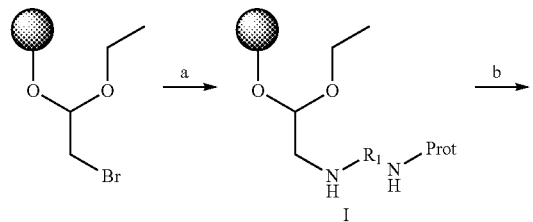

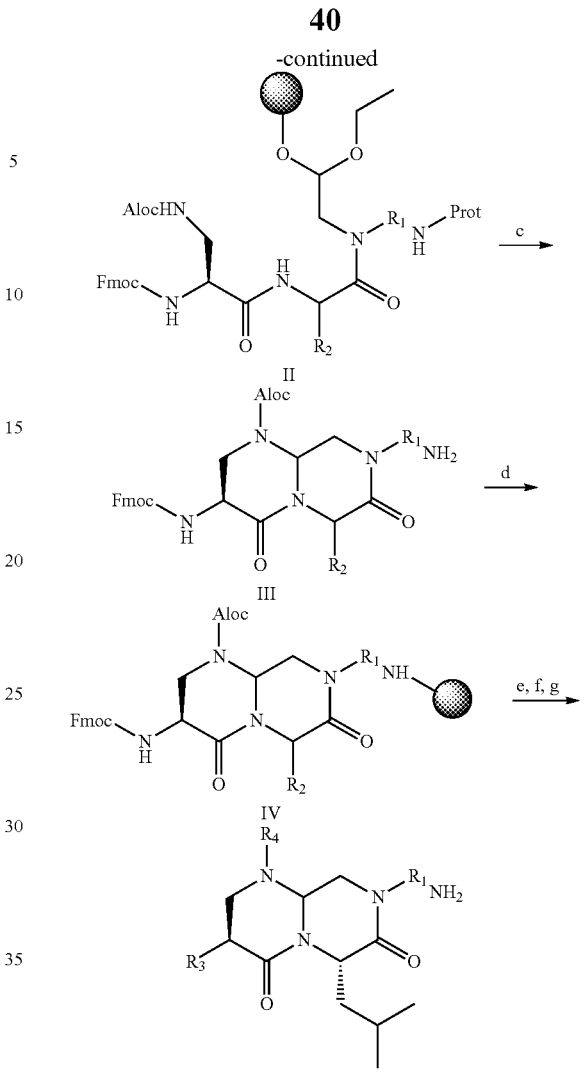

Formula I
(a) 0.5M solution of Protected diamine in DMSO, 60° C., overnight.
(b) (i) Fmoc-R2 aminoacid coupling, TCFH/collidine (II) 10% piperidine in DMF, 20 minutes (iii) Fmoc-Dap(Aloc), DIC/HOBt.
(c) (i) 60% a. formic acid, 4 hrs (ii) column purification.
(d) attachment to the 2-chloro-chlorotrityl resin, 2 eq. In DCM, DIEA.
(e) 10% piperidine in DMF, 20 minutes (ii) 0.5M R3-COOH acid chloride, DCM, collidine, overnight. (f) (i) Pd(0), DCM, dimethylbarbituric acid. (ii) R4-COOH, TCFH, DIEA, DCM.
(g) (i) 95% TFA in DCM, 2% water, 3% EDT, 1 hr. (ii) HPLC purification.

Preferred procedure for preparing cyclic azabicycloalkane structure Formula I involves stepwise synthesis of linear precursor II on a bromoacetal resin and simultaneous cleavage and cyclization off the resin to form protected intermediate III (Scheme A). Acidolabile protecting group (preferred Boc) on amine R1-NH-Prot is cleaved and exposed amine was reattached to a 2-Chloro-chlorotrityl resin to form resin-bound intermediate IV. This intermediate is decorated with R3 and R4 using conventional deprotection/coupling procedures. The final product is cleaved from the resin using strong acid TFA than purified by HPLC.

General Synthetic Scheme B:

Alternative procedure for preparing cyclic azabicycloalkane structure Formula I involves stepwise synthesis of linear precursor IV on a Wang resin and simultaneous acid cleavage and cyclization to form final product formula I (depicted in Scheme B). This approach offered lower yield compare to method A.

41

QC and Purification:

The purity of products was checked by analytical PR-HPLC using a Waters Alliance 2695 Separation Model with a Waters 2487 dual wavelength detector (220 and 280 nm) on a reverse phase column (Waters Symmetry C18, 4.6×75 mm, 3.5 µm). Crude compounds were eluted with a linear gradient of aqueous $CH_3CN/0.1\%$ $CF_3CO_2H$ at a flow rate of 1.0 mL/min.

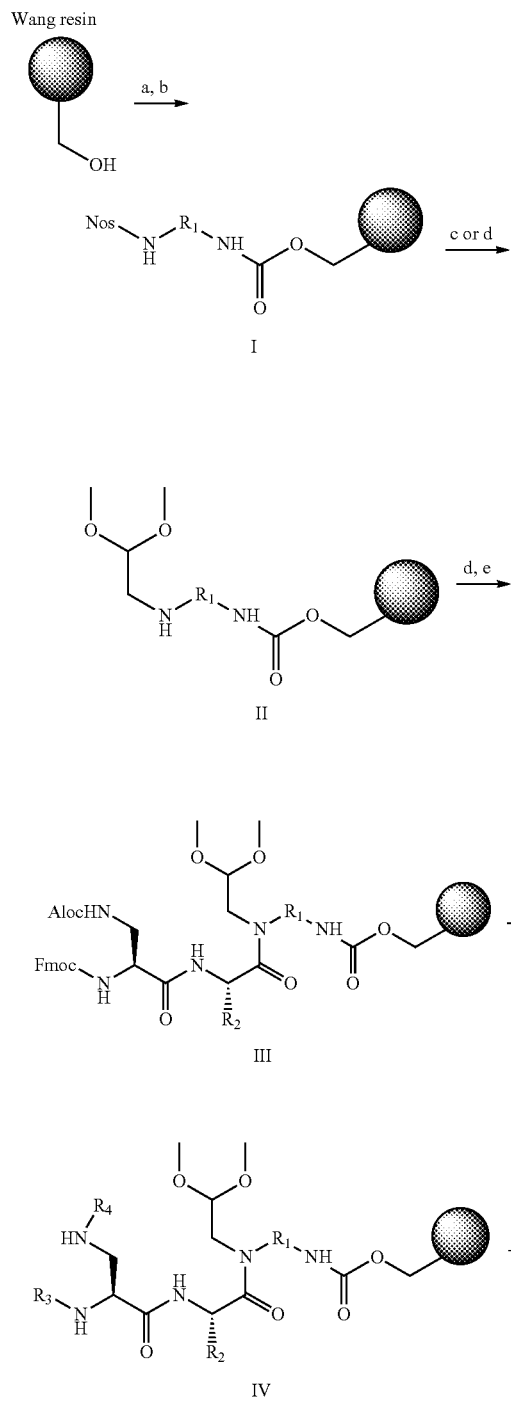

Scheme B. Solid-phase synthesis of compounds Formula I.

42

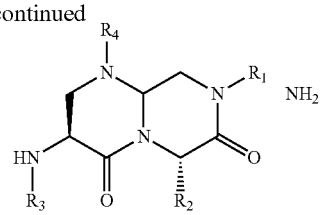

Formula I (a) 0.5M solution of Protected diamine in DMSO, 60° C., overnight. (b) (i) Fmoc-R2 aminoacid coupling, TCFH/collidine (II) 10% piperidine in DMF, 20 minutes (iii) Fmoc-Dap (Aloc), DIC/HOBt. (c) (i) 60% a. formic acid, 4 hrs (ii) column purification. (d) attachment to the 2-Chloro-chlorotrityl resin, 2 eq. In DCM, DIEA. (e) 10% piperidine in DMF, 20 minutes (ii) 0.5 M R3-COOH acid chloride, DCM, collidine, overnight. (f) (i) Pd(0), DCM, dimethylbarbituric acid. (ii) R4-COOH, TCFH, DIEA, DCM. (g) (i) 95% TFA, 2% water, 3% EDT, 1 hr. (ii) HPLC purification.

Purification of compounds was achieved on a Waters 600 HPLC using a reverse phase column (Vydac C18, 15-20 µm, 22×250 mm). Compounds were eluted with a linear gradient of $CH_3CN/0.1\%$ $CF_3CO_2H$ at a flow rate of 5.0 mL/min. Separation was monitored at 230 and 280 nm. Flash chromatography was performed on a borosilicate glass column (2.6×250 mm, Sigma, St. Louis, MO) filled with 60A silicagel (Aldrich). The compounds were eluted with an step gradient flow of EtOAc/MeoH mixtures. Structures were characterized by ESI (Finnigan, Thermoquest LCQ ion trap instrument) or MALDI-TOF (Bruker Reflex-III, α-cyano-cinnamic acid as a matrix). For internal calibration an appropriate mixture of standard peptides was used with an average resolution of 8,000-9,000. High resolution mass measurements were carried out on a FT-ICR IonSpec 4.7T instrument.

Specific Examples of Azabicycloalkanes: C781
(Formula I, Procedure A)

Preparation of the cyclized azabicycloalkanes analogs using the scheme outlined in Scheme 1 will be illustrated by the following non-limiting specific examples:

N-((3S,6S)-1-furan-2-carbonyl)-6-isobutyl-4,7-di-oxo-8-(piperidin-4-ylmethyl)octahydro- Scheme 1. Solid-phase synthesis of C781.

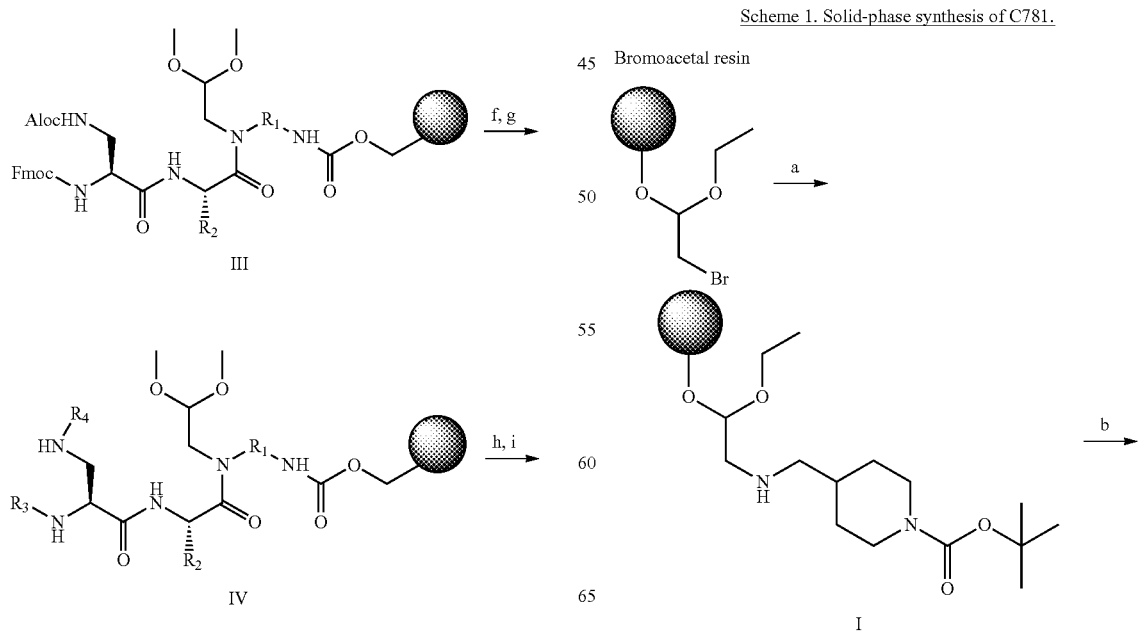

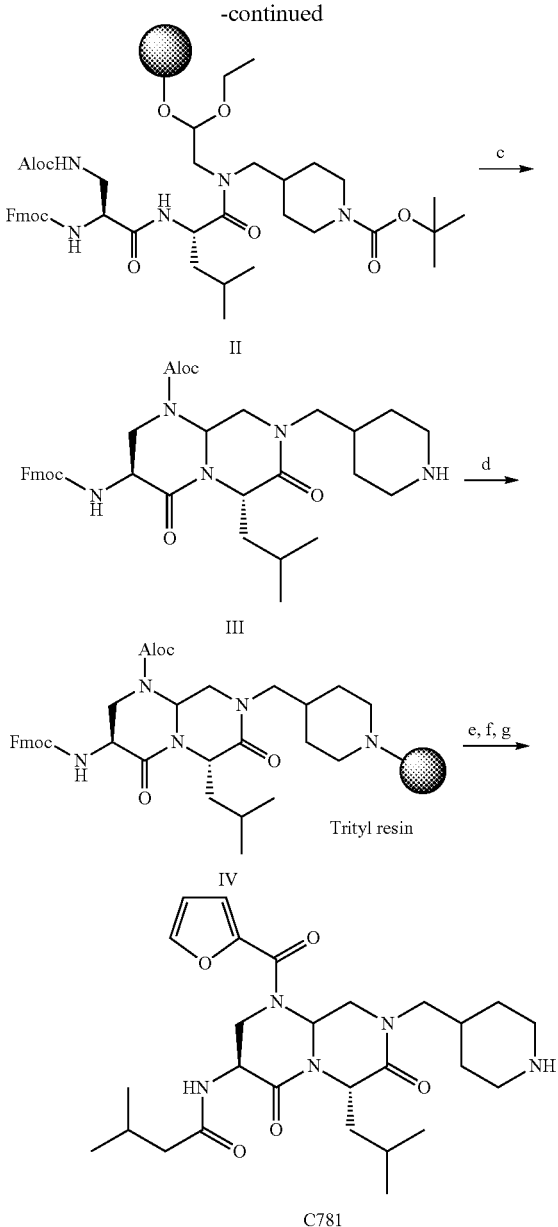

(a) 0.5M solution of Protected diamine in DMSO, 60° C., overnight. (b) (i) Fmoc-Leu coupling, TCFH/collidine (II) 10% piperidine in DMF, 20 minutes (iii) Fmoc-Dap (Aloc), DIC/HOBt. (c) (i) 60% a. formic acid, 4 hrs (ii) column purification. (d) attachment to the 2-Chloro-chlorotrityl resin, 2.5 eq. In DCM, DIEA. (e) 10% piperidine in DMF, 20 minutes (ii) 0.5 M isovarelyl chloride, DCM, collidine, overnight. (f) (i) Pd(0), DCM, dimethylbarbituric acid. (ii) 2-furoic acid, TCFH, DIEA, DCM. (g) (i) 94% TFA in DCM, 3% water, 3% EDT, 1 hr. (ii) HPLC purification.

2H-pyrazino[1,2-a]pyrimidin-3-yl)-3-methylbutane-amide (C781)

Stage 1 (Intermediate I)

The bromoacetal resin (0.2 g, 0.25 mmol) was swelled for 2 hours by the addition of DCM. The swollen resin was carried out through the solid-phase procedure. The resin was washed successively with DMF (3×2 min), DCM (3×2 min), DMSO (5×2 min). Displacement of bromine was accomplished with 0.5M solution of 1-N-Boc-4-(aminomethyl) piperidine (0.214 g, 1 mmol, 4 equiv.) in DMSO at 60° C. overnight. The reaction mixture was removed by filtration and the resin was washed successively with DMSO (5×2 min), DCM (3×2 min). Before coupling of Fmoc-Leu, the resin was neutralized with 10% diisopropylethylamine (DIEA) in DCM, (2×3 min), followed by washing successively with DCM (3×2 min), DMF (5×2 min).

Stage 2 (Intermediate II)

The intermediate resin I from previous step (0.2 g, 0.25 mmol) was coupled with Fmoc-Leu. The coupling was performed by adding Fmoc-Leu (0.353 g, 1 mmol, 4 equiv) and coupling reagents [TCFH (0.28 g, 1 mmol, 4 equiv) and DIEA (0.35 mL, 2 mmol, 8 equiv)] in DMF (2 mL) to the resin and stirring the mixture overnight. The coupling was repeated for 3 hour. The reaction mixture was removed by filtration and the resin was washed successively with DMF (5×2 min), DCM (3×2 min). The $N^{\alpha}$-Fmoc protecting group was removed with 1:10 piperidine in DMF (1×2 min and 1×20 min). The resin was washed successively with DMF (5×2 min), DCM (3×2 min), a solution of 0.05 mM solution of Bromophenol Blue in 0.2 M HOBt in DMF, then DMF. The $N^{\alpha}$-FmocDap(Aloc) was coupled using pre-activated 0.3 M HOBt esters in DMF-DCM mixture (3 equiv of $N^{\alpha}$-Fmoc-Dap(Aloc), 3 equiv of HOBt, and 3 equiv of DIC). The resin slurry was stirred for 2 h or until the bromophenol test became negative (yellow). If the test failed, the resin was washed with DMF and the amino acid was coupled again by the HCTU/2,4,6-lutidine procedure (0.3 M solution of 3 equiv of $N^{\alpha}$-Fmoc amino acid, 3 equiv of HCTU, and 6 equiv of 2,4,6-lutidine in DMF. The reaction mixture was removed by filtration and the resin was washed successively with DMF (5×2 min), DCM (3×2 min), and MeOH (3×2 min). The reactor was placed in vacuum oven to remove solvents.

Stage 3 (Intermediate III)

The dry intermediate resin II from previous step (0.2 g, 0.25 mmol) was treated with 60% a formic acid (2 mL) for 4 hrs. The resin was filtrated and washed with water (2×2 min). Acid filtrate and washes were collected and lyophilized. The crude intermediate III was purified using column chromatography to yield pure III (74 mg, 53%, (M+H)$^+$ 559.3, HPLC>95%).

Stage 4 (Intermediate IV)

The dry intermediate III from previous step (74 mg, 132 μmop was added to dry 2-Chloro-chlorotrityl resin (250 mg, 430 μmol 2.5 eq.). Dry DCM (2.0 mL) and DIEA (171 μL, 1.0 mmol) were injected into the resin and the mixture was agitated at room temperature for overnight. The reaction was quenched by adding methanol (0.2 mL, 30 min). The reaction mixture was removed by filtration and the resin was washed successively with DMF (3×2 min), DCM (5×2 min), and DMF (2×2 min).

Stage 5 (Final Product C781)

The intermediate resin IV was deprotected by piperidine. The $N^{\alpha}$-Fmoc protecting group was removed with 1:10 piperidine in DMF (1×2 min and 1×20 min). The resin was washed successively with DMF (5×2 min), DCM (5×2 min). The isovaleric acid was coupled using 0.3 M acid chloride in DCM (isovaleryl chloride, 121 mg, 1.0 mmol, 7.6 equiv; pyridine, 80 mL, 1.0 mmol, 7.6 equiv). The resin slurry was stirred for 3 h, the reaction mixture removed by filtration, the resin was washed with DCM (5×2 min) and the isovaleric acid was coupled again using 5 equiv. The reaction mixture was removed by filtration and the resin was washed successively with DMF (5×2 min), DCM (3×2 min). The $N^{\alpha}$-Aloc protecting group was removed with Palladium (0) catalyzed cleavage (Tetrakis(triphenylphosphine)palladium(0) (Pd (PPh3)4), 11.5 mg, 0.01 mmol; 1,3-dimethylbarbituric acid, 78 mg, 0.5 mmol) in 0.5 mL DCM then repeated (2×30 min). The resin was washed successively with DCM (3×2 min), DMF (5×2 min), a solution of 0.5 M Sodium Diethyldithiocarbamate trihydrate (113 mg in 1 mL) in DMF (2×10 min), then washed with DMF (5×2 min). The resin was neutralized by 0.5 M DIEA in DMF (5×2 min), then washed with DMF (5×2 min) and DCM (5×2 min). The final coupling of 2-furoic acid was performed by adding 2-furoic acid (112 mg, 1 mmol, 7.6 equiv) and coupling reagents [TCFH (0.28 g, 1 mmol, 7.6 equiv) and DIEA (0.35 mL, 2 mmol, 15.2 equiv)] in DCM (2 mL) to the resin and stirring the mixture overnight. The coupling was repeated for 3 hour using 5 equiv for 2-furoic acid. The reaction mixture was removed by filtration and the resin was washed successively with DMF (5×2 min), DCM (7×2 min), then cleaved by strong acid. A cleavage cocktail (2.0 mL) consisting of $CF_3CO_2H$ (94%), $H_2O$ (3%), and EDT (3%) was injected into the resin and the mixture was agitated at room temperature for 4 h. The solution was filtered, the resin was washed with $CF_3CO_2H$ (2×3 min), the liquid phases were collected and concentrated under a stream of nitrogen, and the product was precipitated using cold $Et_2O$/hexane. The crude product was washed three times with cold $Et_2O$/hexane, lyophilized, HLPC purified, and characterized as described above. The desired product was 25 mg of C781 as a white lyophilizate (yield 19%, $(M+H)^+$ 515.30, HPLC>95%).

$^1$H NMR: 0.86 (d, 6H), 0.90 (d, 6H), 1.30 (m, 4H), 1.60 (m, 1H), 1.74 (t, 2H), 1.97 (m. 1H), 2.0 (d, 2H), 2.02 (m. 1H), 2.81 (m, 4H), 3.3 (t, 2H), 3.50 (t, 2H), 3.70 (m, 2H), 4.5 (t, 1H), 5.0 (t, 1H), 6.10 (t, 1H), 6.7 (t, 1H), 7.30 (d, 1H), 7.92 (d, 1H), 8.25 (d, 1H). 13C NMR: 26.8 (CH3), 27.5 (CH3), 28.3 (CH), 29.5 (CH), 30.7 (CH2), 32.0 ((CH), 32.5 (CH), 48.2 ((CH2), 49.5 (CH2), 52.3 (CH2), 52.8 (CH2), 54.1 (CH2), 58.5 (CH), 114.1 (CH), 117.3 (ArCH), 150.5 (ArCH), 151.5 (ArCH), 164.1 (CO), 170.07 (CO), 172.3 (CO), 177.6 (CO)

Specific Examples of Azabicycloalkanes: C732 (Formula I, Procedure A)

Preparation of the cyclized azabicycloalkane analogs using the scheme outlined in Scheme 2 will be illustrated by the following non-limiting specific examples:

Scheme 2. Solid-phase synthesis of C732.

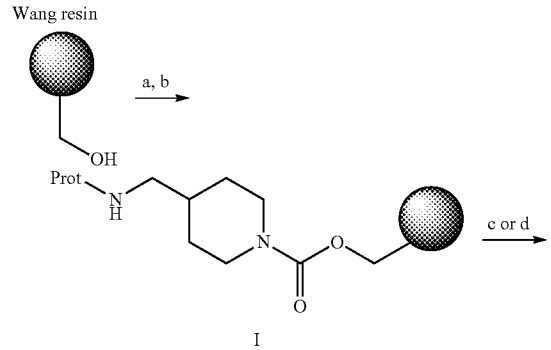

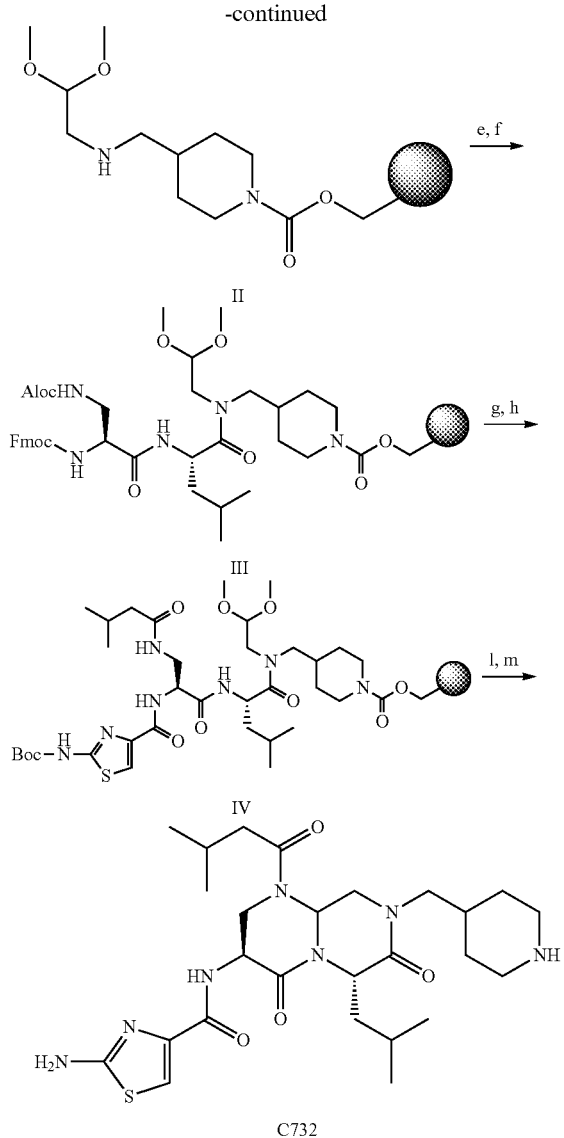

C732
Exact Mass: 547.29

(a) 0.5M solution of DCl in THF, 1 hr. (b) 4-nitro-N-(piperidin-4-ylmethyl)benzenesulfonamide, DIEA, DCM for route c or 4-nitrobenzyl (piperidin-4-ylmethyl) carbamate, DIEA, DCM for route d. (c) (i) 1-bromo-2-dimethoxyethane, DIEA, DMF 60° C.; (ii) DBU, mercaptoethanol in DMF or (d) (i) 4.0 M SnCl2, 0.1M HCl in DMF, 50° C., (ii) 0.5M dimethoxyacetaldehyde in DCM (iii) NaBH3CN in 1% AcOH in DMF. (e) (i) Fmoc-Leu, TCFH/collidine (ii) 10% piperidine in DMF, 20 minutess (f) Fmoc-Dap(Aloc), DIC/HOBt. (g) (i) 10% piperidine in DMF, 20 minutes (ii) (ii) n-Boc-2-aminothiazole-4-carboxylic acid, TCFH, DIEA, DMF. (h) (i) Pd(0), DCM, dimethylbarbituric acid. (ii) 0.5 M isovarelyl chloride, DCM, pyridine. (I) (i) 90% TFA, 10% water for 1 hr; or 60% a. formic acid, 4 hrs. (m) HPLC purification.

2-amino-N-((3S,6S)-6-isobutyl-1-(3-methylbutanoyl)-4,7-dioxo-8-(piperidin-4-ylmethyl)octahydro-2H-pyrazino[1,2-a]pyrimidin-3-ylthiazole-4-carboxamide (C732)

Stage 1 (Intermediate I)

The Wang resin (0.36 g, 0.25 mmol) was swelled for 2 hours by the addition of DCM. The swollen resin was carried out through the solid-phase procedure in plastic syringes using Torviq semiautomatic device. The resin was washed successively with DMF (3×2 min), DCM (3×2 min), THF (5×2 min). Activation of primary alcohol was accomplished with a solution of 1,1'-carbonyldiimidazole (CDI, 0.163 g, 1 mmol, 4 equiv) in 2 mL THF for 1 hr. The reaction mixture was removed by filtration and the resin was washed successively with THF (5×2 min), DCM (7×2 min). Activated resin was treated with 4-nitro-N-(piperidin-4-ylmethyl) benzenesulfonamide (4-(N-Nos-aminomethyl)piperidine, 0.299 g, 1 mmol, 4 equiv) and DIEA (171 mL, 1 mmol, 4 equiv) in THF at room temperature overnight. The reaction mixture was removed by filtration and the resin was washed successively with THF (5×2 min), DCM (3×2 min). The resin was neutralized with 10% DIEA in DCM, (2×3 min), followed by washing successively with DCM (3×2 min), DMF (5×2 min). Alternatively, activated resin was treated with 4-nitrobenzyl(piperidin-4-ylmethyl)carbamate (4-(N-4-pNZ-aminomethyl) piperidine, 0.293 g, 1 mmol, 4 equiv) and DIEA (171 mL, 1 mmol, 4 equiv) in THF at room temperature overnight then washed as described for Nos derivative above.

Stage 2 (Intermediate II)
Route c (Nos Protection):

The intermediate resin I (Nos-protcted) from previous step was alkylated by adding 1-bromo-2-dimethoxyethane (0.170, 1 mmol, 4 equiv) and DIEA (0.35 mL, 2 mmol, 8 equiv) in DMF (2 mL) to the resin and stirring the mixture overnight at 60° C. The alkylation was repeated for 3 hour. The reaction mixture was removed by filtration and the resin was washed successively with DMF (5×2 min), DCM (3×2 min). The N-Nos protecting group was removed with a mixture of 0.7M solution of 2-mercaptoethanol/DBU in DMF (2×10 min). The reaction mixture was removed by filtration and the resin was washed successively with DMF (5×2 min). The resin was neutralized by 0.5 M DIEA in DMF (5×2 min), then washed with DMF (5×2 min) and DCM (5×2 min).

Route d (pNZ Protection):

The intermediate resin I (pNZ protected) from previous step was deprotected. The N-pNZ protecting group was removed with a mixture 4.0 M $SnCl_2$, 0.1M HCl in DMF by stirring the resin at 50° C. (2×30 min).). The reaction mixture was removed by filtration and the resin was washed successively with DMF (5×2 min). The resin was reductively alkylated in two steps. The resin was treated with 0.5M dimethoxyacetaldehyde in DCM (2 mL) for 30 minutes. The reaction mixture was removed by filtration and the resin was washed successively with DCM (5×2 min), DMF (3×2 min), and 1% acetic acid in DMF (3×2 min). The reduction of resin-bound imine was performed by adding Sodium cyanoborohydride (63 mg, 1 mmol, 12 equiv) in 2 mL of 1% acetic acid in DMF overnight. The reaction mixture was removed by filtration and the resin was washed successively with 1% acetic acid in DMF (3×2 min) and DMF (3×2 min). The resin was neutralized by 0.5 M DIEA in DMF (5×2 min), then washed with DMF (5×2 min) and DCM (5×2 min).

Stage 3 (Intermediate III)

The intermediate resin II was coupled with Fmoc-Leu. The coupling was performed by adding Fmoc-Leu (0.353 g, 1 mmol, 4 equiv) and coupling reagents [TCFH (0.28 g, 1 mmol, 4 equiv) and DIEA (0.35 mL, 2 mmol, 8 equiv)] in DMF (2 mL) to the resin and stirring the mixture overnight. The coupling was repeated for 3 hour. The reaction mixture was removed by filtration and the resin was washed successively with DMF (5×2 min), DCM (3×2 min). The $N^\alpha$-Fmoc protecting group was removed with 1:10 piperidine in DMF (1×2 min and 1×20 min). The resin was washed successively with DMF (5×2 min), DCM (3×2 min), a solution of 0.05 mM solution of Bromophenol Blue in 0.2 M HOBt in DMF, then DMF. The $N^\alpha$-FmocDap(Aloc) was coupled using pre-activated 0.3 M HOBt esters in DMF-DCM mixture (3 equiv of $N^\alpha$-Fmoc-Dap(Aloc), 3 equiv of HOBt, and 3 equiv of DIC). The resin slurry was stirred for 2 h or until the bromophenol test became negative. If the test failed, the resin was washed with DMF and the amino acid was coupled again by the HCTU/2,4,6-lutidine procedure (0.3 M solution of 3 equiv of $N^\alpha$-Fmoc amino acid, 3 equiv of HCTU, and 6 equiv of 2,4,6-lutidine in DMF. The reaction mixture was removed by filtration and the resin was washed successively with DMF (5×2 min), DCM (3×2 min), Stage 4 (Intermediate IV)

The intermediate resin IV was deprotected by piperidine. The $N^\alpha$-Fmoc protecting group was removed with 1:10 piperidine in DMF (1×2 min and 1×20 min). The resin was washed successively with DMF (5×2 min), DCM (5×2 min). The N-Boc-2-aminothiazole-4-carboxylic coupling was performed by adding Boc-protected acid (244 mg, 1 mmol, 4.0 equiv) and coupling reagents [TCFH (0.28 g, 1 mmol, 4.0 equiv) and DIEA (0.35 mL, 2 mmol, 8 equiv)] in DCM (2 mL) to the resin and stirring the mixture overnight. The resin slurry was stirred for 3 h, the reaction mixture removed by filtration, the resin was washed with DCM (5×2 min) and the acid was coupled again using 3 equiv. The reaction mixture was removed by filtration and the resin was washed successively with DMF (5×2 min), DCM (3×2 min). The $N^\alpha$-Aloc protecting group was removed with Palladium (0) catalyzed cleavage (Tetrakis(triphenylphosphine)palladium(0) (Pd (PPh3)4), 11.5 mg, 0.01 mmol; 1,3-dimethylbarbituric acid, 78 mg, 0.5 mmol) in 0.5 mL DCM then repeated (2×30 min). The resin was washed successively with DCM (3×2 min), DMF (5×2 min), a solution of 0.5 M Sodium diethyldithiocarbamate trihydrate (113 mg in 1 mL) in DMF (2×10 min), then washed with DMF (5×2 min). The resin was neutralized by 0.5 M DIEA in DMF (5×2 min), then washed with DMF (5×2 min) and DCM (5×2 min). The final coupling of isovaleric acid was performed by adding 0.3 M acid chloride in DCM (isovaleryl chloride, 121 mg, 1.0 mmol, 4 equiv; pyridine, 80 mL, 1.0 mmol, 4 equiv). The resin slurry was stirred for 3 h, the reaction mixture removed by filtration, the resin was washed with DCM (5×2 min) and the isovaleric acid was coupled again using 2 equiv of chloride. The reaction mixture was removed by filtration and the resin was washed successively with DMF (5×2 min), DCM (7×2 min).

Stage 5 (Final Product C781)

A cleavage cocktail (2.0 mL) consisting of 60% aqueous formic acid was injected into the resin and the mixture was agitated at room temperature for 4 h. Alternatively, 90% aqueous TFA was used. The solution was filtered, the resin was washed with cleavage cocktail (2×1 mL), the liquid phases were collected and concentrated under a stream of nitrogen, and the product was precipitated using cold $Et_2O$/hexane. The crude product was washed three times with cold $Et_2O$/hexane, lyophilized, purified, and characterized as described above. The desired product was 4.1 mg of C732 as a white lyophilizate (yield 3%, $(M+H)^+$ 547.30, HPLC>95%).

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes.

Whereas it should read:
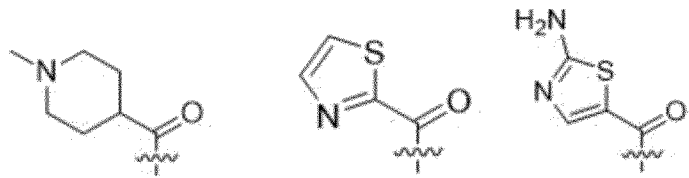
Column 53, Claim 8, Line 66 reads:
comprising one ore more anti-inflammatory agents.
Whereas it should read:
comprising one or more anti-inflammatory agents.
Column 60, Claim 22, Line 60 reads:
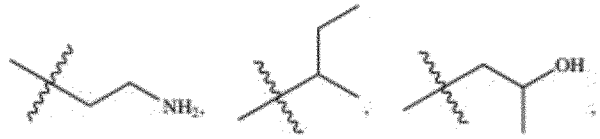
Whereas it should read:
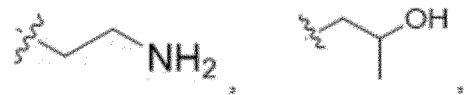
Column 61, Claim 22, Line 20 reads:
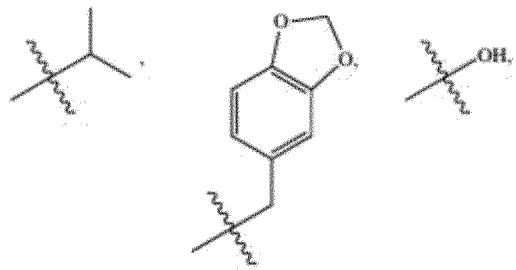
Whereas it should read:
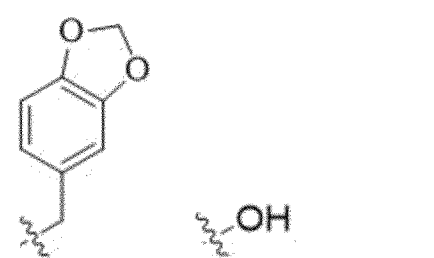

Column 61, Claim 22, Line 55 reads:
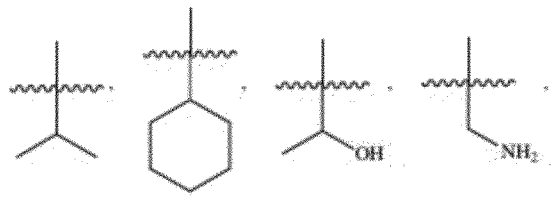
Whereas it should read:
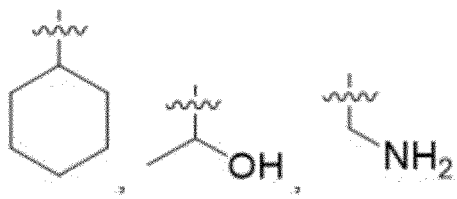
Column 61, Claim 22, Line 65 reads:
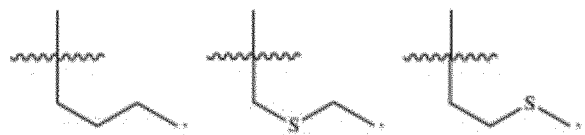
Whereas it should read:
Column 62, Claim 22, Line 10 reads:
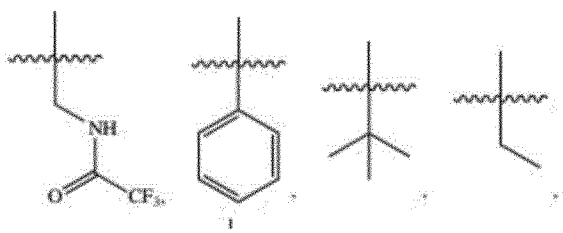
Whereas it should read:
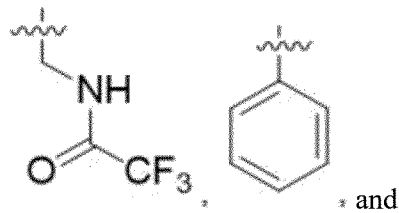, and Column 62, Claim 22, Line 20 reads:
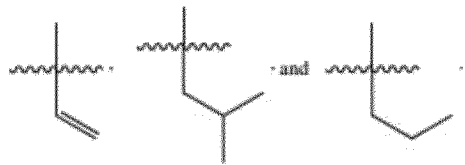
Whereas it should read:

What is claimed is:

1. A composition comprising a compound having a structure encompassed within Formula I,

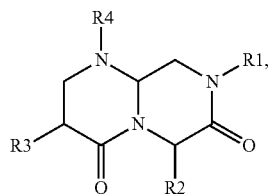

(Formula I)

wherein:

$R_1$ is selected from

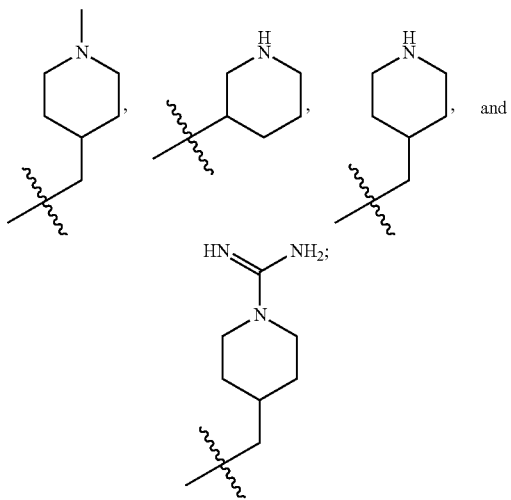

$R_2$ is selected from hydrogen,

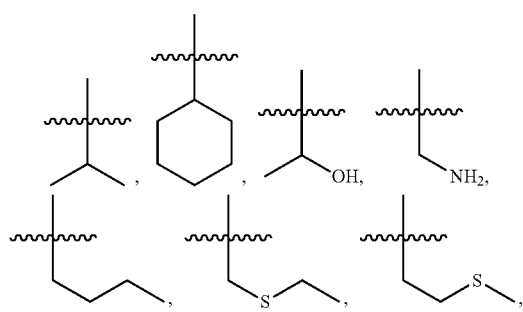

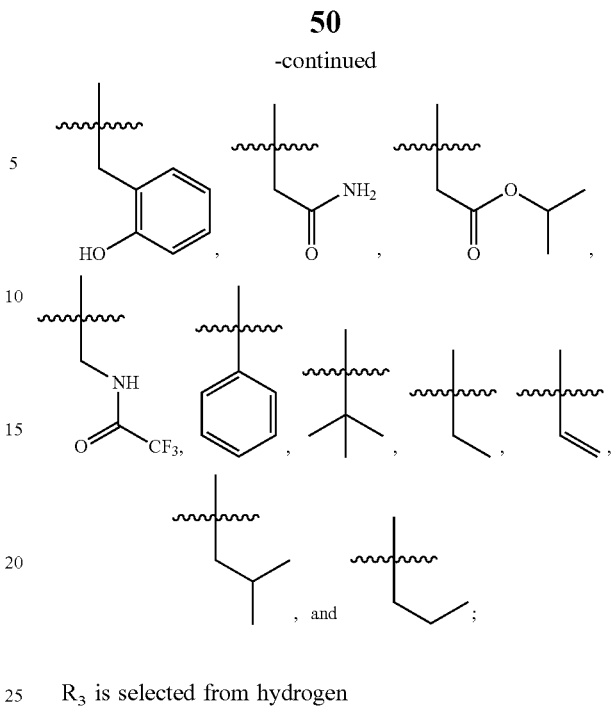

$R_3$ is selected from hydrogen

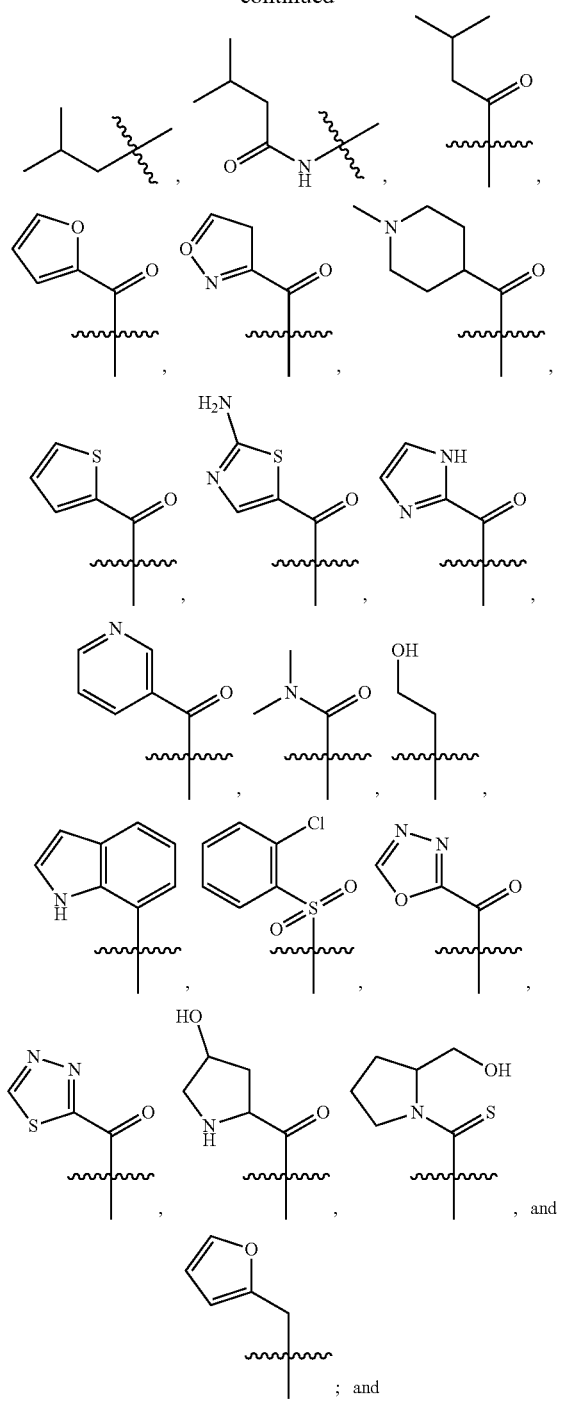
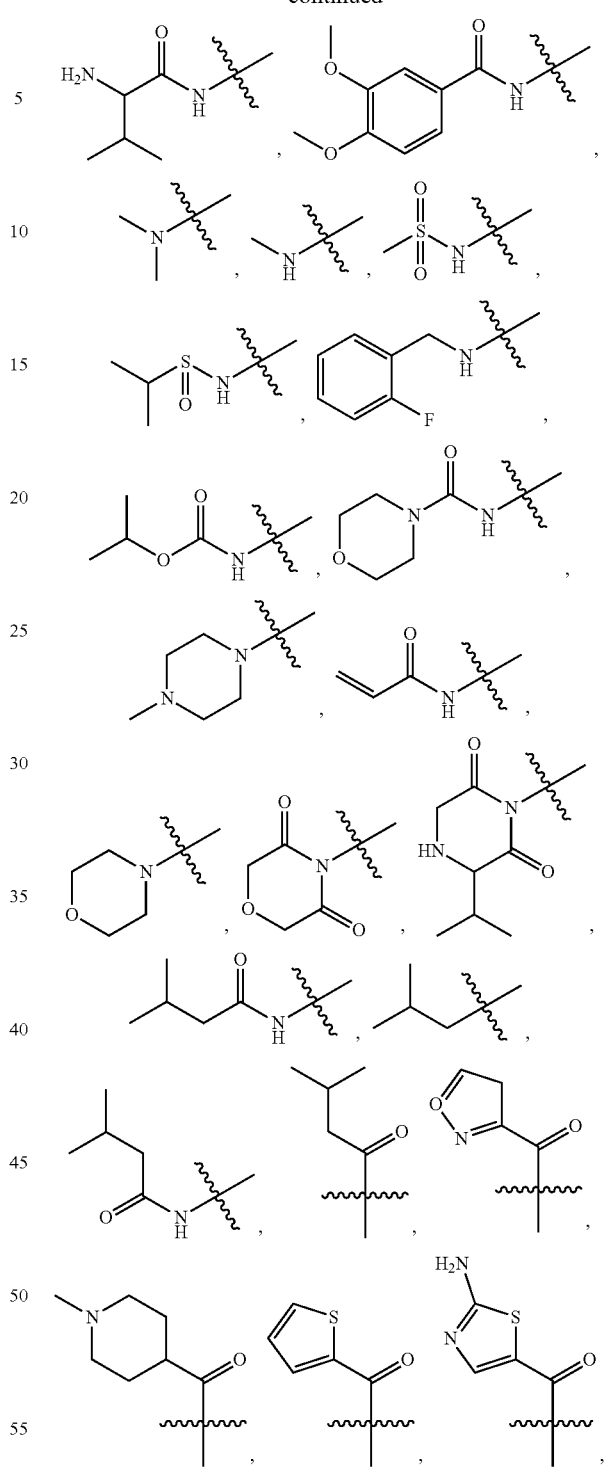
R₄ is selected from hydrogen,
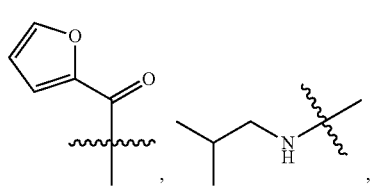

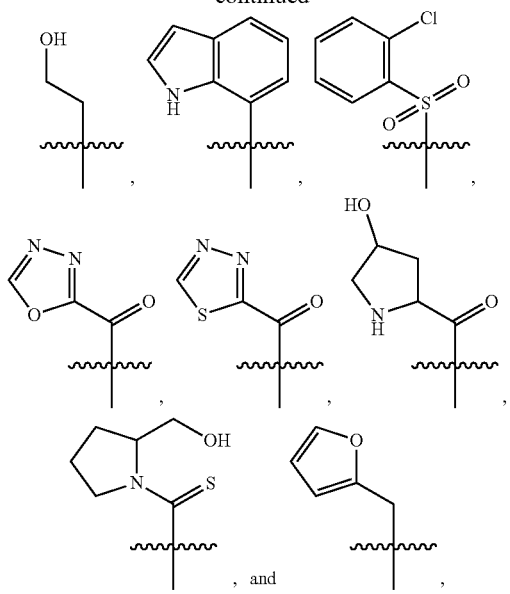

, and or a pharmaceutically acceptable salt, solvate, and/or prodrug thereof; and wherein the resulting compound activates or inhibits $PAR_2$ biological activity.

2. The composition of claim 1, wherein $R_1$ is selected from

3. The composition of claim 1, wherein $R_2$ is

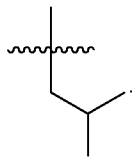 [SMILES: *CC(C)C]

4. The composition of claim 1, wherein neither $R_3$ nor $R_4$ comprise a furoyl moiety.

5. The composition of claim 1, wherein $R_4$ is comprises a heterocyclic ring.

6. A pharmaceutical composition comprising a compound of claim 1.

7. A kit comprising (1) a pharmaceutical composition as recited in claim 6, (2) a container, pack, or dispenser, and (3) instructions for administration.

8. The pharmaceutical composition of claim 6, further comprising one ore more anti-inflammatory agents.

9. The composition of claim 2, wherein $R_1$ is

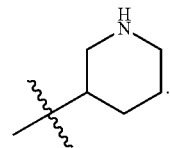 [SMILES: *C1CCCNC1]

10. The composition of claim 4, wherein $R_3$ is selected from hydrogen,

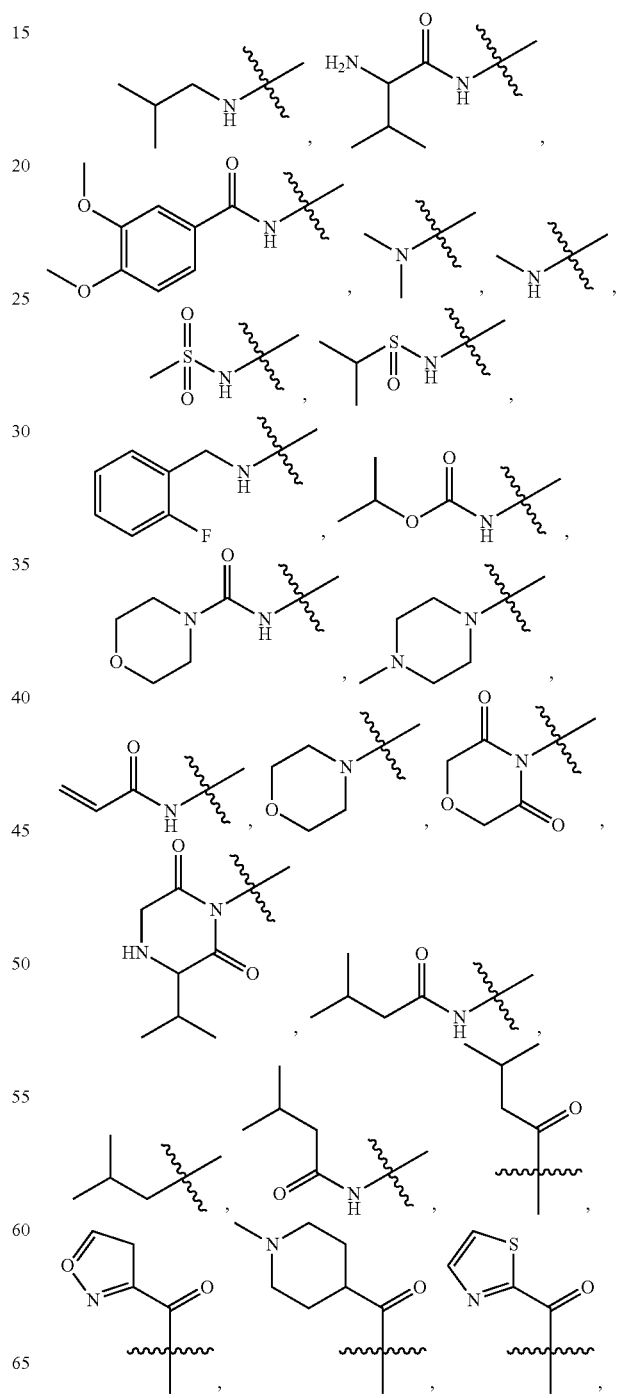

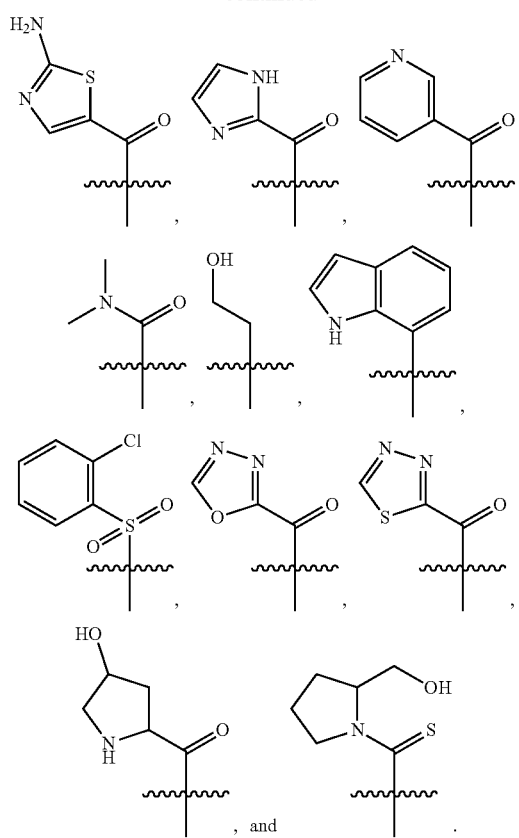
11. The composition of claim 10, wherein R₃ is
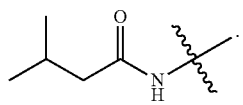 [SMILES: *NC(=O)CC(C)C]
12. The composition of claim 1, wherein R₃ is selected from:
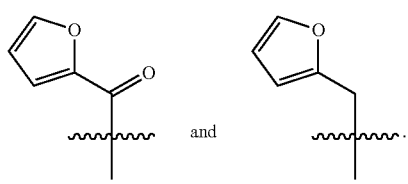 [SMILES: *C(=O)c1ccco1 ; *Cc1ccco1]
13. The composition of claim 4, wherein R₄ is selected from hydrogen,
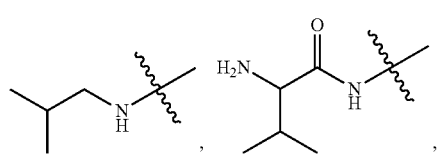
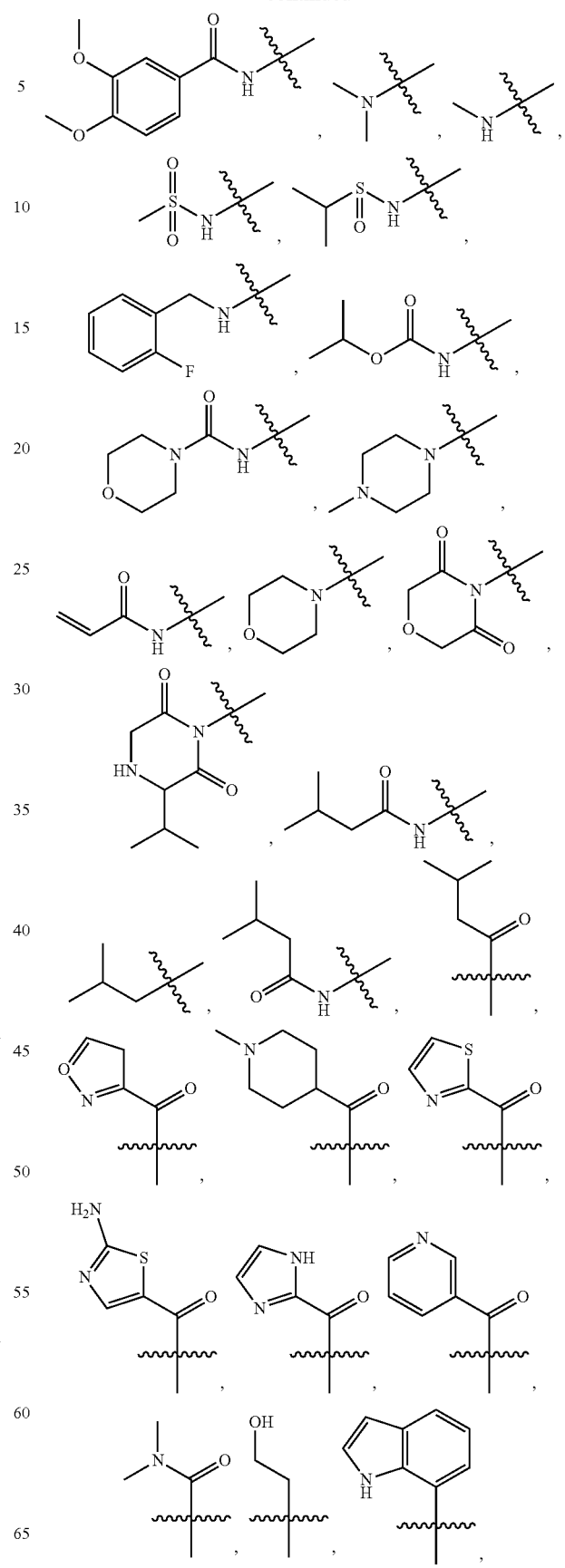

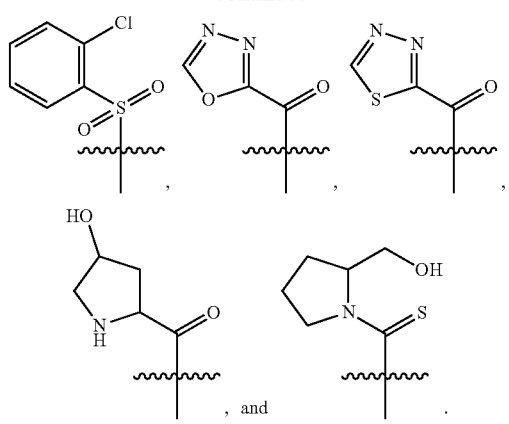
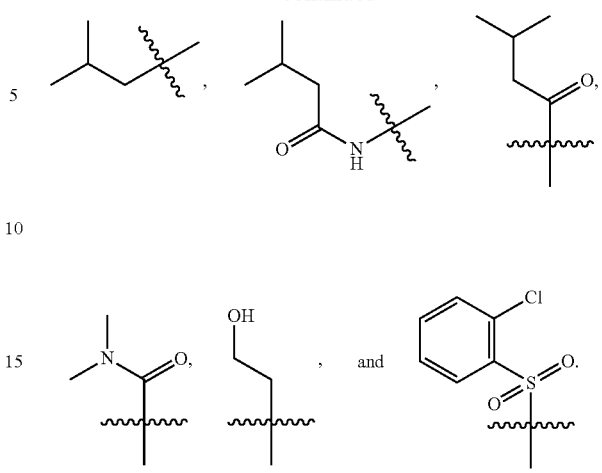
14. The composition of claim 1, wherein $R_4$ is selected from:
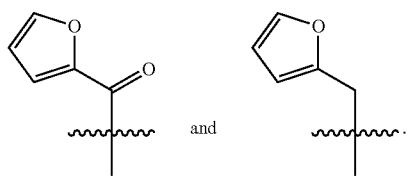 [SMILES: *C(=O)c1ccco1 ; *Cc1ccco1]
15. The composition of claim 1, wherein $R_4$ is selected from:
hydrogen
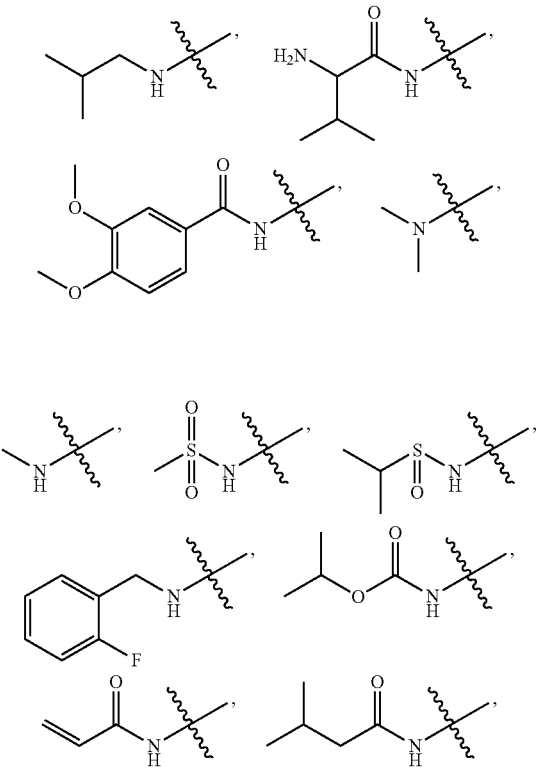
16. The composition of claim 13, wherein $R_4$ is selected from
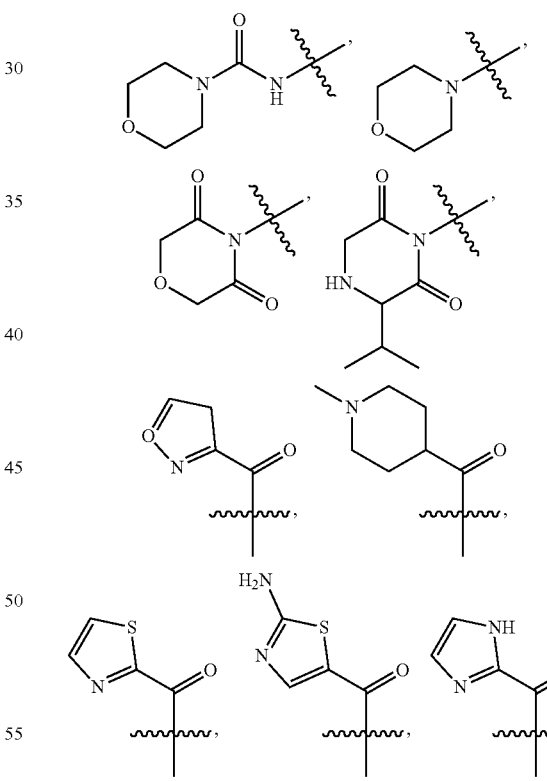
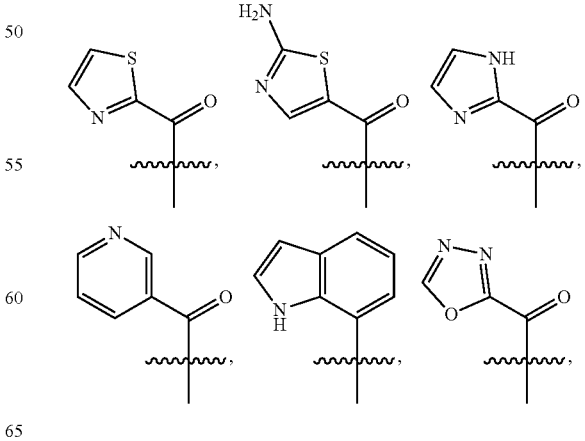

-continued

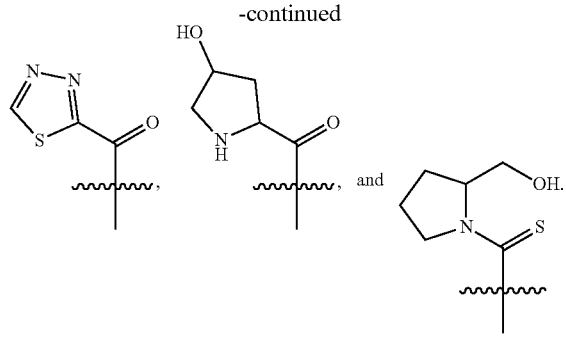

17. The composition of claim 14, wherein R₄ is

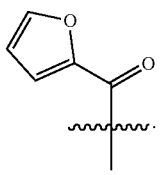

18. The composition of claim 1, wherein the compound is (C732)

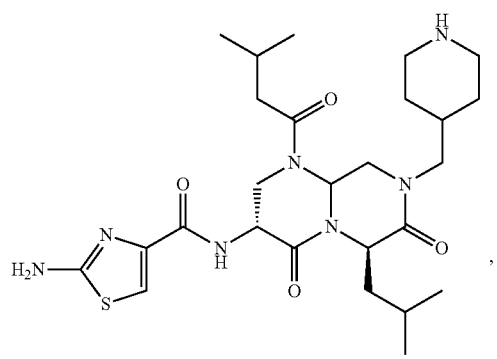

including pharmaceutically acceptable salts, solvates, and/or prodrugs thereof.

19. The composition of claim 18, wherein the compound is (C732)

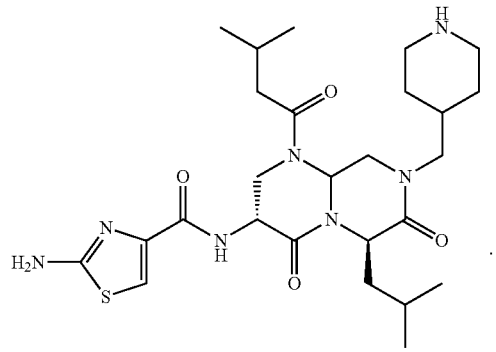

20. The composition of claim 1, wherein the compound is

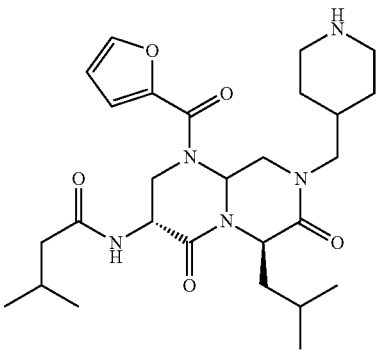

(C781), including pharmaceutically acceptable salts, solvates, and/or prodrugs thereof.

21. The composition of claim 20, wherein the compound is (C781)

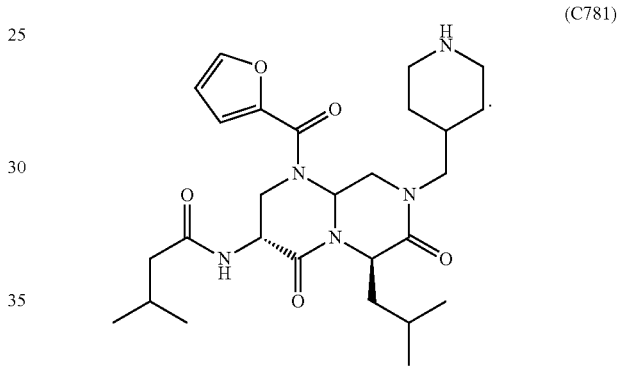

22. A composition comprising a compound having a structure encompassed within Formula I (Formula I)

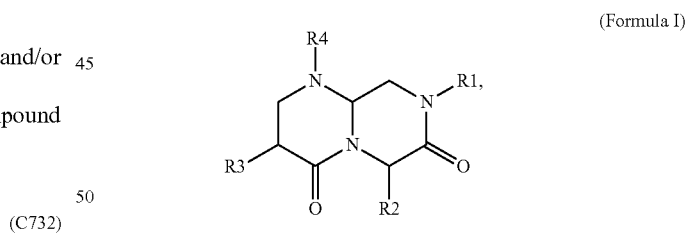

wherein:
R₁ is selected from

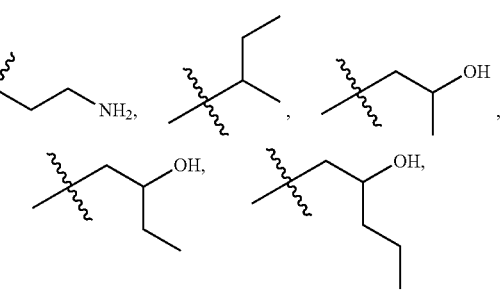

-continued
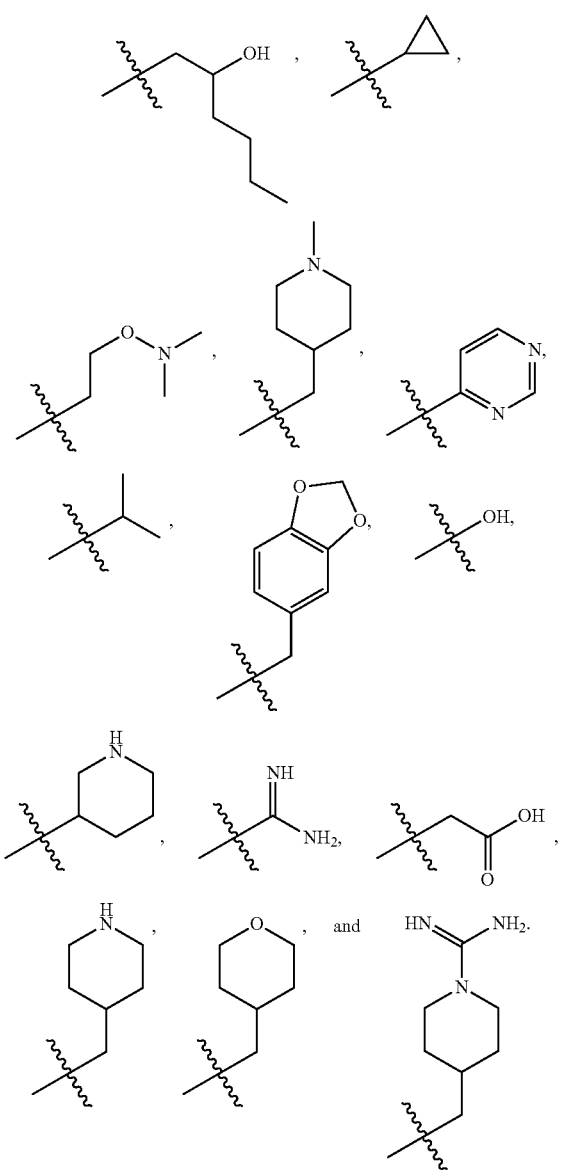
R$_2$ is selected from
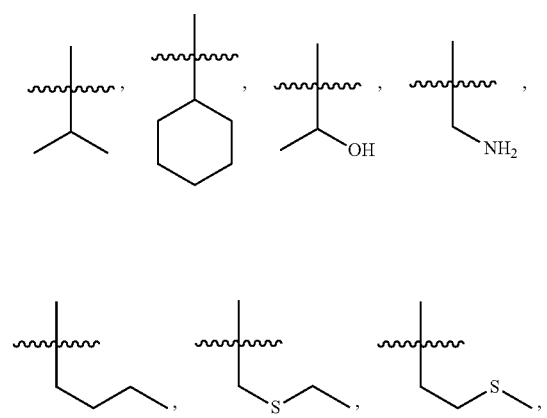
-continued
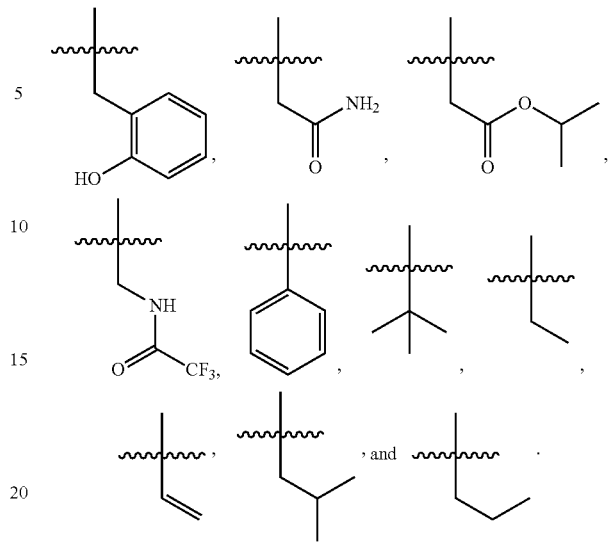
R$_3$ is selected from hydrogen,
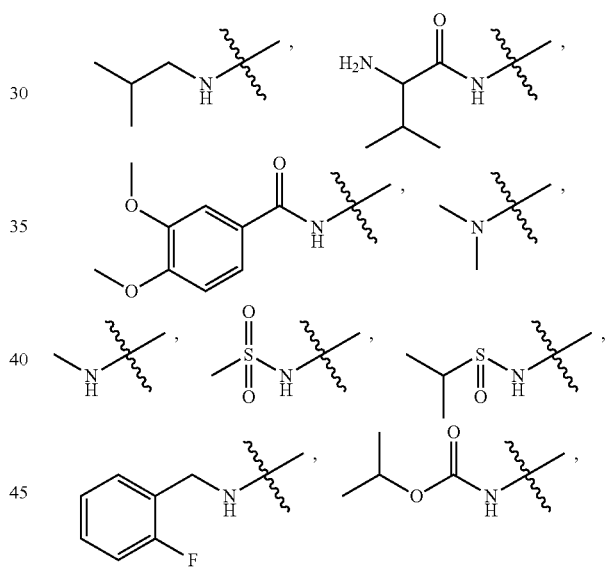
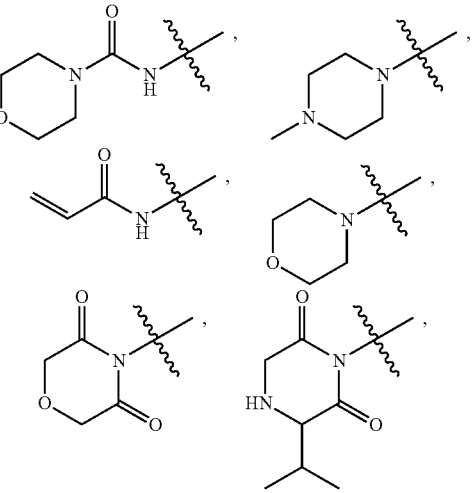

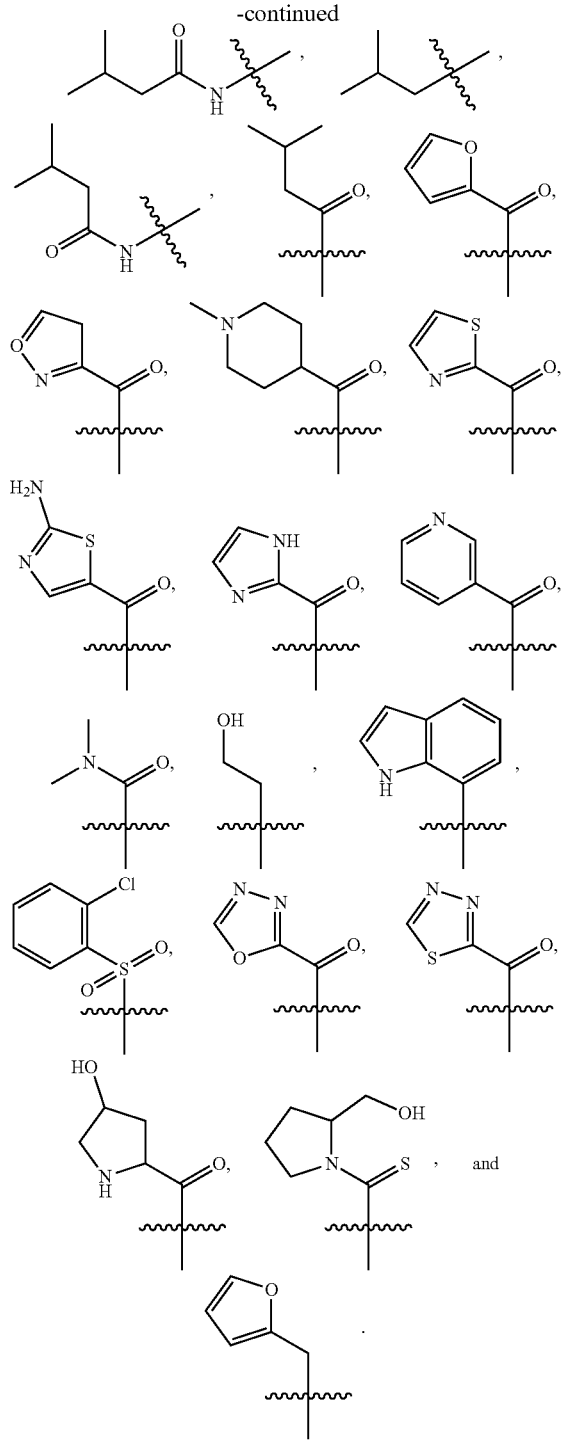
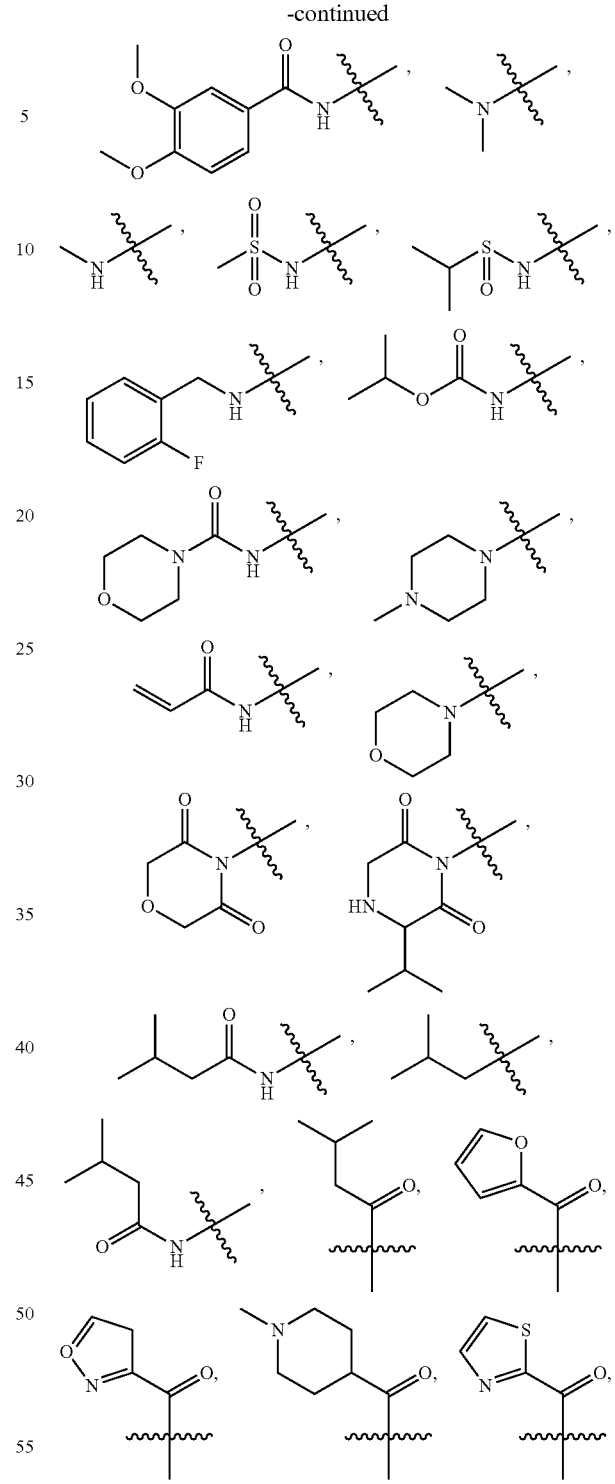
and
R₄ is selected from hydrogen,
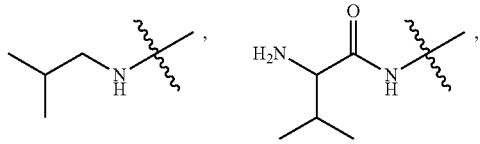

-continued
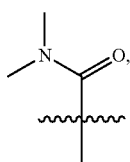 , 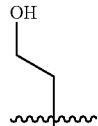 , 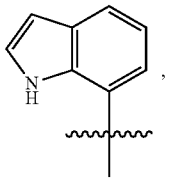 ,
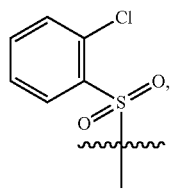 , 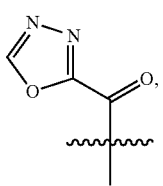 , 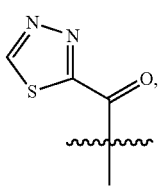 ,
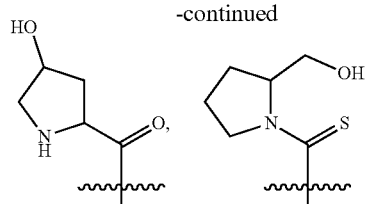
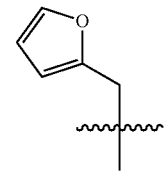
or a pharmaceutically acceptable salt, solvate, and/or prodrug thereof; and
wherein the resulting compound activates or inhibits PAR$_2$ biological activity.
* * * * *

UNITED STATES PATENT AND TRADEMARK OFFICE
CERTIFICATE OF CORRECTION

PATENT NO. : 11,952,379 B2
APPLICATION NO. : 17/046633
DATED : April 9, 2024
INVENTOR(S) : Scott A. Boitano et al.

Page 1 of 4

It is certified that error appears in the above-identified patent and that said Letters Patent is hereby corrected as shown below:

In the Claims

Column 51, Claim 1, Line 20 reads:

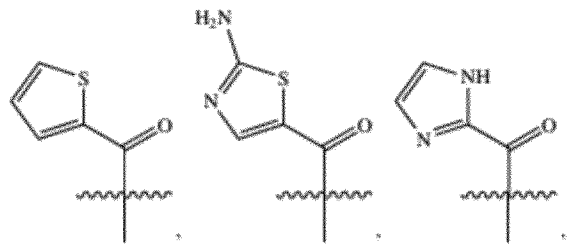

Whereas it should read:

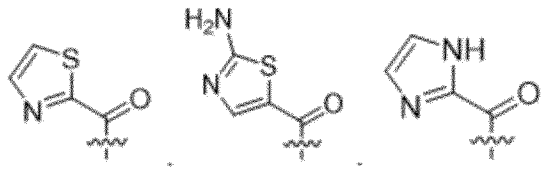

Column 52, Claim 1, Line 50 reads:

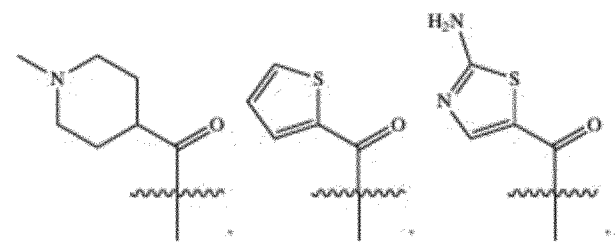

Signed and Sealed this
Second Day of July, 2024

Katherine Kelly Vidal
*Director of the United States Patent and Trademark Office*